(12) United States Patent
Tamarkin et al.

(10) Patent No.: US 8,486,375 B2
(45) Date of Patent: *Jul. 16, 2013

(54) FOAMABLE COMPOSITIONS

(75) Inventors: Dov Tamarkin, Maccabim (IL); Doron Friedman, Karmei Yosef (IL); Meir Eini, Ness Ziona (IL)

(73) Assignee: Foamix Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/400,337

(22) Filed: Feb. 20, 2012

(65) Prior Publication Data

US 2012/0195836 A1 Aug. 2, 2012

Related U.S. Application Data

(60) Continuation of application No. 12/499,609, filed on Jul. 8, 2009, now Pat. No. 8,119,106, which is a division of application No. 10/835,359, filed on Apr. 28, 2004, now Pat. No. 7,575,739.

(60) Provisional application No. 60/466,094, filed on Apr. 28, 2003.

(51) Int. Cl.
*A61K 9/00* (2006.01)
*A61K 9/12* (2006.01)
*A61K 33/18* (2006.01)

(52) U.S. Cl.
USPC ............ 424/45; 424/400; 424/51; 424/78.06; 424/78.07; 514/945; 514/928; 514/828; 514/887

(58) Field of Classification Search
USPC ........ 424/45, 400, 51, 78.06, 78.07; 514/945, 514/928, 887, 828
See application file for complete search history.

(56) References Cited

U.S. PATENT DOCUMENTS

| | | |
|---|---|---|
| 1,159,250 A | 11/1915 | Moulton |
| 1,666,684 A | 4/1928 | Carstens |
| 1,924,972 A | 8/1933 | Beckert |
| 2,085,733 A | 7/1937 | Bird |
| 2,390,921 A | 12/1945 | Clark |
| 2,524,590 A | 10/1950 | Boe |
| 2,586,287 A | 2/1952 | Apperson |
| 2,617,754 A | 11/1952 | Neely |
| 2,767,712 A | 10/1956 | Waterman |
| 2,968,628 A | 1/1961 | Reed |
| 3,004,894 A | 10/1961 | Johnson et al. |
| 3,062,715 A | 11/1962 | Reese et al. |
| 3,067,784 A | 12/1962 | Gorman |
| 3,092,255 A | 6/1963 | Hohman |
| 3,092,555 A | 6/1963 | Horn |
| 3,141,821 A | 7/1964 | Compeau |
| 3,142,420 A | 7/1964 | Gawthrop |
| 3,144,386 A | 8/1964 | Brightenback |
| 3,149,543 A | 9/1964 | Naab |
| 3,154,075 A | 10/1964 | Weckesser |
| 3,178,352 A | 4/1965 | Erickson |
| 3,236,457 A | 2/1966 | Kennedy et al. |
| 3,244,589 A | 4/1966 | Sunnen |
| 3,252,859 A | 5/1966 | Silver |
| 3,261,695 A | 7/1966 | Sienkiewicz |
| 3,263,867 A | 8/1966 | Lehmann |
| 3,263,869 A | 8/1966 | Corsette |
| 3,298,919 A | 1/1967 | Bishop et al. |
| 3,301,444 A | 1/1967 | Wittke |
| 3,303,970 A | 2/1967 | Breslau et al. |
| 3,330,730 A | 7/1967 | Hernandez |
| 3,333,333 A | 8/1967 | Noack |
| 3,346,451 A | 10/1967 | Collins et al. |
| 3,366,494 A | 1/1968 | Bower et al. |
| 3,369,034 A | 2/1968 | Chalmers |
| 3,377,004 A | 4/1968 | Wittke |
| 3,384,541 A | 5/1968 | Clark et al. |
| 3,395,214 A | 7/1968 | Mummert |
| 3,395,215 A | 7/1968 | Schubert |
| 3,401,849 A | 9/1968 | Weber, III |
| 3,419,658 A | 12/1968 | Sanders |
| 3,456,052 A | 7/1969 | Gordon |
| 3,527,559 A | 9/1970 | Sliwinski |
| 3,540,448 A | 11/1970 | Sunnen |
| 3,559,890 A | 2/1971 | Brooks et al. |
| 3,561,262 A | 2/1971 | Borucki |
| 3,563,098 A | 2/1971 | Weber, III |
| 3,574,821 A | 4/1971 | Pfirrmann |
| 3,577,518 A | 5/1971 | Shepherd |
| 3,667,461 A | 6/1972 | Zamarra |

(Continued)

FOREIGN PATENT DOCUMENTS

| | | |
|---|---|---|
| AU | 198780257 | 9/1986 |
| CA | 2422244 | 9/2003 |

(Continued)

OTHER PUBLICATIONS

U.S. Appl. No. 60/789,186, filed Apr. 4, 2006, Tamarkin.

(Continued)

*Primary Examiner* — Mina Haghighatian
(74) *Attorney, Agent, or Firm* — Fish & Richardson P.C.

(57) ABSTRACT

The present invention is related to a foamable composition of matter comprising iodine, water, a foam adjuvant, a surface-active agent and a gelling agent. This foamable composition, which may be provided in a propellant free foaming device, or alternatively may further comprise a propellant, evolves into foam, which is effective in the topical treatment and prevention of various skin disorders.

22 Claims, 1 Drawing Sheet

U.S. PATENT DOCUMENTS

| | | |
|---|---|---|
| 3,751,562 A | 8/1973 | Nichols |
| 3,770,648 A | 11/1973 | Mackles |
| 3,787,566 A | 1/1974 | Gauvreau |
| 3,819,524 A | 6/1974 | Schubert et al. |
| 3,841,525 A | 10/1974 | Siegel |
| 3,849,580 A | 11/1974 | Weinstein et al. |
| 3,865,275 A | 2/1975 | De Nunzio |
| 3,866,800 A | 2/1975 | Schmitt |
| 3,882,228 A | 5/1975 | Boncey et al. |
| 3,886,084 A | 5/1975 | Vassiliades |
| 3,890,305 A | 6/1975 | Weber et al. |
| 3,912,665 A | 10/1975 | Spitzer et al. |
| 3,923,970 A | 12/1975 | Breuer |
| 3,929,985 A | 12/1975 | Webb, Jr. |
| 3,952,916 A | 4/1976 | Phillips |
| 3,959,160 A | 5/1976 | Horsler et al. |
| 3,962,150 A | 6/1976 | Viola |
| 3,963,833 A | 6/1976 | DeSalva et al. |
| 3,966,090 A | 6/1976 | Prussin et al. |
| 3,966,632 A | 6/1976 | Colliopoulos et al. |
| 3,970,219 A | 7/1976 | Spitzer et al. |
| 3,970,584 A | 7/1976 | Hart et al. |
| 3,993,224 A | 11/1976 | Harrison |
| 3,997,467 A | 12/1976 | Jederstrom |
| 4,001,391 A | 1/1977 | Feinstone et al. |
| 4,001,442 A | 1/1977 | Stahlberger et al. |
| 4,018,396 A | 4/1977 | Shoemaker et al. |
| 4,019,657 A | 4/1977 | Spitzer et al. |
| 4,083,974 A | 4/1978 | Turi |
| 4,102,995 A | 7/1978 | Hebborn |
| 4,110,426 A | 8/1978 | Barnhurst et al. |
| 4,124,149 A | 11/1978 | Spitzer et al. |
| 4,145,411 A | 3/1979 | Mende |
| 4,151,272 A | 4/1979 | Geary et al. |
| 4,160,827 A | 7/1979 | Cho et al. |
| 4,213,979 A | 7/1980 | Levine |
| 4,214,000 A | 7/1980 | Papa |
| 4,226,344 A | 10/1980 | Booth et al. |
| 4,229,432 A | 10/1980 | Geria |
| 4,230,701 A | 10/1980 | Holick et al. |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,292,250 A | 9/1981 | DeLuca et al. |
| 4,292,326 A | 9/1981 | Nazzaro-Porro et al. |
| 4,299,826 A | 11/1981 | Luedders |
| 4,305,936 A | 12/1981 | Klein |
| 4,309,995 A | 1/1982 | Sacco |
| 4,310,510 A | 1/1982 | Sherman et al. |
| 4,323,694 A | 4/1982 | Scala, Jr. |
| 4,325,939 A | 4/1982 | Shah |
| 4,329,990 A | 5/1982 | Sneider |
| 4,335,120 A | 6/1982 | Holick et al. |
| 4,352,808 A | 10/1982 | Rane et al. |
| 4,385,161 A | 5/1983 | Caunt et al. |
| 4,386,104 A | 5/1983 | Nazzaro-Porro |
| 4,393,066 A | 7/1983 | Garrett et al. |
| 4,427,670 A | 1/1984 | Ofuchi et al. |
| 4,439,416 A | 3/1984 | Cordon et al. |
| 4,439,441 A | 3/1984 | Hallesy et al. |
| 4,440,320 A | 4/1984 | Wernicke |
| 4,447,486 A | 5/1984 | Hoppe et al. |
| 4,469,674 A | 9/1984 | Shah et al. |
| 4,508,705 A | 4/1985 | Chaudhuri et al. |
| 4,522,948 A | 6/1985 | Walker |
| 4,529,601 A | 7/1985 | Broberg et al. |
| 4,529,605 A | 7/1985 | Lynch et al. |
| 4,552,872 A | 11/1985 | Cooper et al. |
| 4,574,052 A | 3/1986 | Gupte et al. |
| 4,576,961 A | 3/1986 | Lorck et al. |
| 4,595,526 A | 6/1986 | Lai |
| 4,603,812 A | 8/1986 | Stoesser et al. |
| 4,627,973 A | 12/1986 | Moran et al. |
| 4,628,063 A | 12/1986 | Haines et al. |
| 4,661,524 A | 4/1987 | Thomson et al. |
| 4,672,078 A | 6/1987 | Sakai et al. |
| 4,673,569 A | 6/1987 | Shernov et al. |
| 4,678,463 A | 7/1987 | Millar |
| 4,701,320 A | 10/1987 | Hasegawa et al. |
| 4,725,609 A | 2/1988 | Kull, Jr. et al. |
| 4,738,396 A | 4/1988 | Doi et al. |
| 4,741,855 A | 5/1988 | Grote et al. |
| 4,752,465 A | 6/1988 | Mackles |
| 4,770,634 A | 9/1988 | Pellico |
| 4,780,309 A | 10/1988 | Geria et al. |
| 4,784,842 A | 11/1988 | London et al. |
| 4,792,062 A | 12/1988 | Goncalves |
| 4,798,682 A | 1/1989 | Ansmann |
| 4,804,674 A | 2/1989 | Curtis-Prior et al. |
| 4,806,262 A | 2/1989 | Snyder |
| 4,808,388 A | 2/1989 | Beutler et al. |
| 4,822,613 A | 4/1989 | Rodero |
| 4,822,614 A | 4/1989 | Rodero |
| 4,826,048 A | 5/1989 | Skorka et al. |
| 4,827,378 A | 5/1989 | Gillan et al. |
| 4,828,837 A | 5/1989 | Uster et al. |
| 4,836,217 A | 6/1989 | Fischer et al. |
| 4,837,019 A | 6/1989 | Georgalas et al. |
| 4,837,378 A | 6/1989 | Borgman |
| 4,844,902 A | 7/1989 | Grohe |
| 4,847,068 A | 7/1989 | Dole et al. |
| 4,849,117 A | 7/1989 | Bronner et al. |
| 4,855,294 A | 8/1989 | Patel et al. |
| 4,863,900 A | 9/1989 | Pollock et al. |
| 4,867,967 A | 9/1989 | Crutcher |
| 4,873,078 A | 10/1989 | Edmundson et al. |
| 4,874,794 A | 10/1989 | Katz |
| 4,877,805 A | 10/1989 | Kligman |
| 4,885,282 A | 12/1989 | Thornfeldt |
| 4,897,262 A | 1/1990 | Nandagiri et al. |
| 4,902,281 A | 2/1990 | Avoy |
| 4,906,453 A | 3/1990 | Tsoucalas |
| 4,913,893 A | 4/1990 | Varco et al. |
| 4,919,934 A | 4/1990 | Deckner et al. |
| 4,954,487 A | 9/1990 | Cooper et al. |
| 4,956,049 A | 9/1990 | Bernheim et al. |
| 4,957,732 A | 9/1990 | Grollier et al. |
| 4,963,351 A | 10/1990 | Weston |
| 4,966,779 A | 10/1990 | Kirk |
| 4,970,067 A | 11/1990 | Panandiker et al. |
| 4,975,466 A | 12/1990 | Bottcher et al. |
| 4,981,367 A | 1/1991 | Brazelton |
| 4,981,677 A | 1/1991 | Thau |
| 4,981,679 A | 1/1991 | Briggs et al. |
| 4,981,845 A | 1/1991 | Pereira et al. |
| 4,985,459 A | 1/1991 | Sunshine et al. |
| 4,992,478 A | 2/1991 | Geria |
| 4,993,496 A | 2/1991 | Riedle et al. |
| 5,002,540 A | 3/1991 | Brodman et al. |
| 5,002,680 A | 3/1991 | Schmidt et al. |
| 5,007,556 A | 4/1991 | Lover |
| 5,013,297 A | 5/1991 | Cattanach |
| 5,015,471 A | 5/1991 | Birtwistle et al. |
| 5,019,375 A | 5/1991 | Tanner et al. |
| 5,034,220 A | 7/1991 | Helioff et al. |
| 5,035,895 A | 7/1991 | Shibusawa et al. |
| 5,053,228 A | 10/1991 | Mori et al. |
| 5,071,648 A | 12/1991 | Rosenblatt |
| 5,071,881 A | 12/1991 | Parfondry et al. |
| 5,073,371 A | 12/1991 | Turner et al. |
| 5,082,651 A | 1/1992 | Healey et al. |
| 5,087,618 A | 2/1992 | Bodor |
| 5,089,252 A | 2/1992 | Grollier et al. |
| 5,091,111 A | 2/1992 | Neumiller |
| 5,094,853 A | 3/1992 | Hagarty |
| 5,100,917 A | 3/1992 | Flynn et al. |
| 5,104,645 A | 4/1992 | Cardin et al. |
| 5,112,359 A | 5/1992 | Murphy et al. |
| 5,114,718 A | 5/1992 | Damani |
| 5,122,519 A | 6/1992 | Ritter |
| 5,130,121 A | 7/1992 | Kopolow et al. |
| 5,133,972 A | 7/1992 | Ferrini et al. |
| 5,135,915 A | 8/1992 | Czarniecki et al. |
| 5,137,714 A | 8/1992 | Scott |

| Patent No. | Date | Inventor(s) |
|---|---|---|
| 5,143,717 A | 9/1992 | Davis |
| 5,156,765 A | 10/1992 | Smrt |
| 5,164,357 A | 11/1992 | Bartman et al. |
| 5,164,367 A | 11/1992 | Pickart |
| 5,167,950 A | 12/1992 | Lins |
| 5,171,577 A | 12/1992 | Griat et al. |
| 5,196,405 A | 3/1993 | Packman |
| 5,204,093 A | 4/1993 | Victor |
| 5,208,031 A | 5/1993 | Kelly |
| 5,217,707 A | 6/1993 | Szabo et al. |
| 5,219,877 A | 6/1993 | Shah et al. |
| 5,221,696 A | 6/1993 | Ke et al. |
| 5,230,897 A | 7/1993 | Griffin et al. |
| 5,236,707 A | 8/1993 | Stewart, II |
| 5,252,246 A | 10/1993 | Ding et al. |
| 5,254,334 A | 10/1993 | Ramirez et al. |
| 5,262,407 A | 11/1993 | Leveque et al. |
| 5,266,592 A | 11/1993 | Grub et al. |
| 5,279,819 A | 1/1994 | Hayes |
| 5,286,475 A | 2/1994 | Louvet et al. |
| 5,300,286 A | 4/1994 | Gee |
| 5,301,841 A | 4/1994 | Fuchs |
| 5,308,643 A | 5/1994 | Osipow et al. |
| 5,314,904 A | 5/1994 | Egidio et al. |
| 5,322,683 A | 6/1994 | Mackles et al. |
| 5,326,557 A | 7/1994 | Glover et al. |
| 5,344,051 A | 9/1994 | Brown |
| 5,346,135 A | 9/1994 | Vincent |
| 5,352,437 A | 10/1994 | Nakagawa et al. |
| 5,369,131 A | 11/1994 | Poli et al. |
| 5,378,451 A | 1/1995 | Gorman et al. |
| 5,378,730 A | 1/1995 | Lee et al. |
| 5,380,761 A | 1/1995 | Szabo et al. |
| 5,384,308 A | 1/1995 | Henkin |
| 5,385,943 A | 1/1995 | Nazzaro-Porro |
| 5,389,676 A | 2/1995 | Michaels |
| 5,397,312 A | 3/1995 | Rademaker et al. |
| 5,398,846 A | 3/1995 | Corba et al. |
| 5,399,205 A | 3/1995 | Shinohara et al. |
| 5,411,992 A | 5/1995 | Eini et al. |
| 5,422,361 A | 6/1995 | Munayyer et al. |
| 5,429,815 A | 7/1995 | Faryniarz et al. |
| 5,435,996 A | 7/1995 | Glover et al. |
| 5,447,725 A | 9/1995 | Damani et al. |
| 5,449,520 A | 9/1995 | Frigerio et al. |
| 5,451,404 A | 9/1995 | Furman |
| 5,482,965 A | 1/1996 | Rajadhyaksha |
| 5,491,245 A | 2/1996 | Gruning et al. |
| 5,500,211 A | 3/1996 | George et al. |
| 5,508,033 A | 4/1996 | Briand et al. |
| 5,512,555 A | 4/1996 | Waldstreicher |
| 5,514,367 A | 5/1996 | Lentini et al. |
| 5,514,369 A | 5/1996 | Salka et al. |
| 5,520,918 A | 5/1996 | Smith |
| 5,523,078 A | 6/1996 | Baylin |
| 5,527,534 A | 6/1996 | Myhling |
| 5,527,822 A | 6/1996 | Scheiner |
| 5,529,770 A | 6/1996 | McKinzie et al. |
| 5,531,703 A | 7/1996 | Skwarek et al. |
| 5,534,261 A | 7/1996 | Rodgers et al. |
| 5,536,743 A | 7/1996 | Borgman |
| 5,540,853 A | 7/1996 | Trinh et al. |
| 5,545,401 A | 8/1996 | Shanbrom |
| 5,567,420 A | 10/1996 | McEleney et al. |
| 5,576,016 A | 11/1996 | Amselem et al. |
| 5,578,315 A | 11/1996 | Chien et al. |
| 5,585,104 A | 12/1996 | Ha et al. |
| 5,589,157 A | 12/1996 | Hatfield |
| 5,589,515 A | 12/1996 | Suzuki et al. |
| 5,597,560 A | 1/1997 | Bergamini et al. |
| 5,603,940 A | 2/1997 | Candau et al. |
| 5,605,679 A | 2/1997 | Hansenne et al. |
| 5,608,119 A | 3/1997 | Amano et al. |
| 5,611,463 A | 3/1997 | Favre |
| 5,612,056 A | 3/1997 | Jenner et al. |
| 5,613,583 A | 3/1997 | Kono et al. |
| 5,613,623 A | 3/1997 | Hildebrandt |
| 5,614,171 A | 3/1997 | Clavenna et al. |
| 5,614,178 A | 3/1997 | Bloom et al. |
| 5,635,469 A | 6/1997 | Fowler et al. |
| 5,641,480 A | 6/1997 | Vermeer |
| 5,643,600 A | 7/1997 | Mathur |
| 5,645,842 A | 7/1997 | Gruning et al. |
| 5,650,554 A | 7/1997 | Moloney |
| 5,658,575 A | 8/1997 | Ribier et al. |
| 5,658,749 A | 8/1997 | Thornton |
| 5,658,956 A | 8/1997 | Martin et al. |
| 5,663,208 A | 9/1997 | Martin |
| 5,672,634 A | 9/1997 | Tseng et al. |
| 5,679,324 A | 10/1997 | Lisboa et al. |
| 5,683,710 A | 11/1997 | Akemi et al. |
| 5,686,088 A | 11/1997 | Mitra et al. |
| 5,693,258 A | 12/1997 | Tonomura et al. |
| 5,695,551 A | 12/1997 | Buckingham et al. |
| 5,700,396 A | 12/1997 | Suzuki et al. |
| 5,716,611 A | 2/1998 | Oshlack et al. |
| 5,716,621 A | 2/1998 | Bello |
| 5,719,122 A | 2/1998 | Chiodini et al. |
| 5,719,197 A | 2/1998 | Kanios et al. |
| 5,725,872 A | 3/1998 | Stamm et al. |
| 5,725,874 A | 3/1998 | Oda |
| 5,730,964 A | 3/1998 | Waldstreicher |
| 5,733,558 A | 3/1998 | Breton et al. |
| 5,733,572 A | 3/1998 | Unger et al. |
| 5,747,049 A | 5/1998 | Tominaga |
| 5,753,241 A | 5/1998 | Ribier et al. |
| 5,753,245 A | 5/1998 | Fowler et al. |
| 5,759,520 A | 6/1998 | Sachetto |
| 5,759,579 A | 6/1998 | Singh et al. |
| 5,767,104 A | 6/1998 | Bar-Shalom et al. |
| 5,773,410 A | 6/1998 | Yamamoto |
| 5,783,202 A | 7/1998 | Tomlinson et al. |
| 5,788,664 A | 8/1998 | Scalise |
| 5,792,448 A | 8/1998 | Dubief et al. |
| 5,792,922 A | 8/1998 | Moloney et al. |
| 5,797,955 A | 8/1998 | Walters |
| 5,804,546 A | 9/1998 | Hall et al. |
| 5,817,322 A | 10/1998 | Xu et al. |
| 5,824,650 A | 10/1998 | De Lacharriere et al. |
| 5,833,960 A | 11/1998 | Gers-Barlag et al. |
| 5,833,961 A | 11/1998 | Siegfried et al. |
| 5,837,270 A | 11/1998 | Burgess |
| 5,840,744 A | 11/1998 | Borgman |
| 5,840,771 A | 11/1998 | Oldham et al. |
| 5,843,411 A | 12/1998 | Hernandez et al. |
| 5,846,983 A | 12/1998 | Sandborn et al. |
| 5,849,042 A | 12/1998 | Lim et al. |
| 5,856,452 A | 1/1999 | Moloney et al. |
| 5,858,371 A | 1/1999 | Singh et al. |
| 5,865,347 A | 2/1999 | Welschoff |
| 5,866,040 A | 2/1999 | Nakama et al. |
| 5,869,529 A | 2/1999 | Sintov et al. |
| 5,871,720 A | 2/1999 | Gutierrez et al. |
| 5,877,216 A | 3/1999 | Place et al. |
| 5,879,469 A | 3/1999 | Avram et al. |
| 5,881,493 A | 3/1999 | Restive |
| 5,885,581 A | 3/1999 | Massand |
| 5,889,028 A | 3/1999 | Sandborn et al. |
| 5,889,054 A | 3/1999 | Yu et al. |
| 5,891,458 A | 4/1999 | Britton et al. |
| 5,902,574 A | 5/1999 | Stoner et al. |
| 5,902,789 A | 5/1999 | Stoltz |
| 5,905,092 A | 5/1999 | Osborne et al. |
| 5,910,382 A | 6/1999 | Goodenough et al. |
| 5,911,981 A | 6/1999 | Dahms et al. |
| 5,912,007 A | 6/1999 | Pan et al. |
| 5,914,122 A | 6/1999 | Otterbeck et al. |
| 5,914,310 A | 6/1999 | Li et al. |
| 5,922,331 A | 7/1999 | Mausner |
| 5,925,669 A | 7/1999 | Katz et al. |
| 5,948,682 A | 9/1999 | Moloney |
| 5,951,544 A | 9/1999 | Konwitz |
| 5,951,989 A | 9/1999 | Heymann |
| 5,951,993 A | 9/1999 | Scholz et al. |
| 5,952,373 A | 9/1999 | Lanzendorfer et al. |
| 5,952,392 A | 9/1999 | Katz et al. |
| 5,955,414 A | 9/1999 | Brown et al. |
| 5,959,161 A | 9/1999 | Kenmochi et al. |

| | | | | | | |
|---|---|---|---|---|---|---|
| 5,961,957 | A | 10/1999 | McAnalley | 6,403,061 | B1 | 6/2002 | Candau et al. |
| 5,961,998 | A | 10/1999 | Arnaud et al. | 6,403,069 | B1 | 6/2002 | Chopra et al. |
| 5,972,310 | A | 10/1999 | Sachetto | 6,410,036 | B1 | 6/2002 | De Rosa et al. |
| 5,976,555 | A | 11/1999 | Liu et al. | 6,423,323 | B2 | 7/2002 | Neubourg |
| 5,980,904 | A | 11/1999 | Leverett et al. | 6,428,772 | B1 | 8/2002 | Singh et al. |
| 5,990,100 | A | 11/1999 | Rosenberg et al. | 6,433,003 | B1 | 8/2002 | Bobrove et al. |
| 5,993,846 | A | 11/1999 | Friedman et al. | 6,433,024 | B1 | 8/2002 | Popp et al. |
| 6,001,341 | A | 12/1999 | Genova et al. | 6,433,033 | B1 | 8/2002 | Isobe et al. |
| 6,006,948 | A | 12/1999 | Auer | 6,437,006 | B1 | 8/2002 | Yoon et al. |
| 6,019,967 | A | 2/2000 | Breton et al. | 6,440,429 | B1 | 8/2002 | Torizuka et al. |
| 6,024,942 | A | 2/2000 | Tanner et al. | 6,447,801 | B1 | 9/2002 | Salafsky et al. |
| 6,030,630 | A | 2/2000 | Fleury et al. | 6,455,076 | B1 | 9/2002 | Hahn et al. |
| 6,033,647 | A | 3/2000 | Touzan et al. | 6,468,989 | B1 | 10/2002 | Chang et al. |
| 6,039,936 | A | 3/2000 | Restle et al. | 6,479,058 | B1 | 11/2002 | McCadden |
| 6,042,848 | A | 3/2000 | Lawyer et al. | 6,486,168 | B1 | 11/2002 | Skwierczynski et al. |
| 6,045,779 | A | 4/2000 | Mueller et al. | 6,488,947 | B1 | 12/2002 | Bekele |
| 6,071,536 | A | 6/2000 | Suzuki et al. | 6,511,655 | B1 | 1/2003 | Muller et al. |
| 6,075,056 | A | 6/2000 | Quigley, Jr. et al. | 6,514,487 | B1 | 2/2003 | Barr |
| 6,080,394 | A | 6/2000 | Lin et al. | 6,524,594 | B1 | 2/2003 | Santora et al. |
| 6,087,317 | A | 7/2000 | Gee | 6,531,118 | B1 | 3/2003 | Gonzalez et al. |
| 6,090,772 | A | 7/2000 | Kaiser et al. | 6,534,455 | B1 | 3/2003 | Maurin et al. |
| 6,093,408 | A | 7/2000 | Hasenoehrl et al. | 6,536,629 | B2 | 3/2003 | van der Heijden |
| 6,096,756 | A | 8/2000 | Crain et al. | 6,544,530 | B1 | 4/2003 | Friedman |
| 6,110,477 | A | 8/2000 | Hernandez et al. | 6,544,562 | B2 | 4/2003 | Singh et al. |
| 6,110,966 | A | 8/2000 | Pollock | 6,547,063 | B1 | 4/2003 | Zaveri et al. |
| 6,113,888 | A | 9/2000 | Castro et al. | 6,548,074 | B1 | 4/2003 | Mohammadi |
| 6,116,466 | A | 9/2000 | Gueret | 6,562,355 | B1 | 5/2003 | Renault |
| 6,121,210 | A | 9/2000 | Taylor | 6,566,350 | B2 | 5/2003 | Ono et al. |
| 6,126,920 | A | 10/2000 | Jones et al. | 6,582,679 | B2 | 6/2003 | Stein et al. |
| 6,140,355 | A | 10/2000 | Egidio et al. | 6,582,710 | B2 | 6/2003 | Deckers et al. |
| 6,146,645 | A | 11/2000 | Deckers et al. | 6,589,509 | B2 | 7/2003 | Keller et al. |
| 6,146,664 | A | 11/2000 | Siddiqui | 6,596,287 | B2 | 7/2003 | Deckers et al. |
| 6,162,834 | A | 12/2000 | Sebillotte-Arnaud et al. | 6,599,513 | B2 | 7/2003 | Deckers et al. |
| 6,165,455 | A | 12/2000 | Torgerson et al. | 6,620,773 | B1 | 9/2003 | Stork et al. |
| 6,168,576 | B1 | 1/2001 | Reynolds | 6,638,981 | B2 | 10/2003 | Williams et al. |
| 6,171,347 | B1 | 1/2001 | Kunz et al. | 6,649,571 | B1 | 11/2003 | Morgan |
| 6,180,669 | B1 | 1/2001 | Tamarkin | 6,649,574 | B2 | 11/2003 | Cardis et al. |
| 6,183,762 | B1 | 2/2001 | Deckers et al. | 6,672,483 | B1 | 1/2004 | Roy |
| 6,186,367 | B1 | 2/2001 | Harrold | 6,682,726 | B1 | 1/2004 | Marchesi et al. |
| 6,187,290 | B1 | 2/2001 | Gilchrist et al. | 6,691,898 | B2 | 2/2004 | Hurray et al. |
| 6,189,810 | B1 | 2/2001 | Nerushai et al. | 6,709,663 | B2 | 3/2004 | Espinoza |
| 6,190,365 | B1 | 2/2001 | Abbott et al. | 6,723,309 | B1 | 4/2004 | Deane |
| 6,204,285 | B1 | 3/2001 | Fabiano et al. | 6,730,288 | B1 | 5/2004 | Abram |
| 6,210,656 | B1 | 4/2001 | Touzan et al. | 6,753,000 | B2 | 6/2004 | Breton et al. |
| 6,210,742 | B1 | 4/2001 | Deckers et al. | 6,753,167 | B2 | 6/2004 | Moloney et al. |
| 6,214,318 | B1 | 4/2001 | Osipow et al. | 6,762,158 | B2 | 7/2004 | Lukenbach et al. |
| 6,214,788 | B1 | 4/2001 | Velazco et al. | 6,765,001 | B2 | 7/2004 | Gans et al. |
| 6,221,381 | B1 | 4/2001 | Shelford et al. | 6,774,114 | B2 | 8/2004 | Castiel et al. |
| 6,221,823 | B1 | 4/2001 | Crisanti et al. | 6,777,591 | B1 | 8/2004 | Chaudhary et al. |
| 6,224,888 | B1 | 5/2001 | Vatter et al. | 6,790,435 | B1 | 9/2004 | Ma et al. |
| 6,231,837 | B1 | 5/2001 | Stroud et al. | 6,796,973 | B1 | 9/2004 | Contente et al. |
| 6,232,315 | B1 | 5/2001 | Shafer et al. | RE38,623 | E | 10/2004 | Hernandez et al. |
| 6,251,369 | B1 | 6/2001 | Stoltz | 6,811,767 | B1 | 11/2004 | Bosch et al. |
| 6,258,374 | B1 | 7/2001 | Friess et al. | 6,834,778 | B2 | 12/2004 | Jinbo et al. |
| 6,271,295 | B1 | 8/2001 | Powell et al. | 6,843,390 | B1 | 1/2005 | Bristor |
| 6,274,150 | B1 | 8/2001 | Simonnet et al. | 6,875,438 | B2 | 4/2005 | Kraemer et al. |
| 6,287,546 | B1 | 9/2001 | Reich et al. | 6,881,271 | B2 | 4/2005 | Ochiai |
| 6,294,550 | B1 | 9/2001 | Place et al. | 6,890,567 | B2 | 5/2005 | Nakatsu et al. |
| 6,299,023 | B1 | 10/2001 | Arnone | 6,902,737 | B2 | 6/2005 | Quemin et al. |
| 6,299,032 | B1 | 10/2001 | Hamilton | 6,911,211 | B2 | 6/2005 | Eini et al. |
| 6,299,900 | B1 | 10/2001 | Reed et al. | 6,946,120 | B2 | 9/2005 | Wai-Chiu So et al. |
| 6,305,578 | B1 | 10/2001 | Hildebrandt et al. | 6,946,139 | B2 | 9/2005 | Henning |
| 6,306,841 | B1 | 10/2001 | Place et al. | 6,951,654 | B2 | 10/2005 | Malcolm et al. |
| 6,308,863 | B1 | 10/2001 | Harman | 6,955,816 | B2 | 10/2005 | Klysz |
| 6,319,913 | B1 | 11/2001 | Mak et al. | 6,956,062 | B2 | 10/2005 | Beilfuss et al. |
| 6,328,950 | B1 | 12/2001 | Franzke et al. | 6,958,154 | B2 | 10/2005 | Andolino Brandt et al. |
| 6,328,982 | B1 | 12/2001 | Shiroyama et al. | 6,967,023 | B1 | 11/2005 | Eini et al. |
| 6,333,362 | B1 | 12/2001 | Lorant | 6,968,982 | B1 | 11/2005 | Burns |
| 6,335,022 | B1 | 1/2002 | Simonnet et al. | 6,969,521 | B1 | 11/2005 | Gonzalez et al. |
| 6,341,717 | B2 | 1/2002 | Auer | RE38,964 | E | 1/2006 | Shillington |
| 6,344,218 | B1 | 2/2002 | Dodd et al. | 6,994,863 | B2 | 2/2006 | Eini et al. |
| 6,348,229 | B1 | 2/2002 | Eini et al. | 7,002,486 | B2 | 2/2006 | Lawrence |
| 6,358,541 | B1 | 3/2002 | Goodman | 7,014,844 | B2 | 3/2006 | Mahalingam et al. |
| 6,364,854 | B1 | 4/2002 | Ferrer et al. | 7,021,499 | B2 | 4/2006 | Hansen et al. |
| 6,372,234 | B1 | 4/2002 | Deckers et al. | 7,029,659 | B2 | 4/2006 | Abram |
| 6,375,960 | B1 | 4/2002 | Simonnet et al. | 7,060,253 | B1 | 6/2006 | Mundschenk |
| 6,383,471 | B1 | 5/2002 | Chen et al. | 7,078,058 | B2 | 7/2006 | Jones et al. |
| 6,395,258 | B1 | 5/2002 | Steer | 7,083,799 | B1 | 8/2006 | Giacomoni |
| 6,395,300 | B1 | 5/2002 | Straub et al. | 7,137,536 | B2 | 11/2006 | Walters et al. |

| | | |
|---|---|---|
| 7,195,135 B1 | 3/2007 | Garcia |
| 7,222,802 B2 | 5/2007 | Sweeton |
| 7,225,518 B2 | 6/2007 | Eidenschink et al. |
| 7,226,230 B2 | 6/2007 | Liberatore |
| 7,235,251 B2 | 6/2007 | Hamer et al. |
| 7,270,828 B2 | 9/2007 | Masuda et al. |
| 7,455,195 B2 | 11/2008 | Mekata |
| 7,497,354 B2 | 3/2009 | Decottignies et al. |
| 7,575,739 B2 * | 8/2009 | Tamarkin et al. ............... 424/43 |
| 7,645,803 B2 | 1/2010 | Tamarkin et al. |
| 7,654,415 B2 | 2/2010 | van der Heijden |
| 7,682,623 B2 | 3/2010 | Eini et al. |
| 7,700,076 B2 | 4/2010 | Tamarkin et al. |
| 7,704,518 B2 * | 4/2010 | Tamarkin et al. ............ 424/405 |
| 7,793,807 B2 | 9/2010 | Goujon et al. |
| 7,820,145 B2 | 10/2010 | Tamarkin et al. |
| 7,960,416 B2 | 6/2011 | Sato et al. |
| 8,119,106 B2 * | 2/2012 | Tamarkin et al. ............... 424/45 |
| 2001/0006654 A1 | 7/2001 | Cannell et al. |
| 2001/0027218 A1 | 10/2001 | Stern et al. |
| 2001/0027981 A1 | 10/2001 | Yquel |
| 2001/0036450 A1 | 11/2001 | Verite et al. |
| 2002/0002151 A1 | 1/2002 | Ono et al. |
| 2002/0004063 A1 | 1/2002 | Zhang |
| 2002/0013481 A1 | 1/2002 | Schonrock et al. |
| 2002/0015721 A1 | 2/2002 | Simonnet et al. |
| 2002/0032171 A1 | 3/2002 | Chen et al. |
| 2002/0035046 A1 | 3/2002 | Lukenbach et al. |
| 2002/0035070 A1 | 3/2002 | Gardlik et al. |
| 2002/0035087 A1 | 3/2002 | Barclay |
| 2002/0035182 A1 | 3/2002 | L'Alloret et al. |
| 2002/0039591 A1 | 4/2002 | Dahle |
| 2002/0044659 A1 | 4/2002 | Ohta |
| 2002/0045659 A1 | 4/2002 | Michelet et al. |
| 2002/0048798 A1 | 4/2002 | Avery et al. |
| 2002/0058010 A1 | 5/2002 | Picard-Lesboueyries et al. |
| 2002/0072544 A1 | 6/2002 | Miller et al. |
| 2002/0090386 A1 | 7/2002 | Halswanter et al. |
| 2002/0098215 A1 | 7/2002 | Douin et al. |
| 2002/0111281 A1 | 8/2002 | Vishnupad |
| 2002/0117516 A1 | 8/2002 | Lasserre et al. |
| 2002/0134376 A1 | 9/2002 | Castro et al. |
| 2002/0136755 A1 | 9/2002 | Tyrrell et al. |
| 2002/0143188 A1 | 10/2002 | Garvey et al. |
| 2002/0153390 A1 | 10/2002 | Vlodek |
| 2002/0165170 A1 | 11/2002 | Wilson et al. |
| 2002/0182162 A1 | 12/2002 | Shahinpoor et al. |
| 2002/0187181 A1 | 12/2002 | Godbey et al. |
| 2002/0198136 A1 | 12/2002 | Mak et al. |
| 2003/0006193 A1 | 1/2003 | Ikeda et al. |
| 2003/0031693 A1 | 2/2003 | Breton et al. |
| 2003/0053961 A1 | 3/2003 | Eccard |
| 2003/0077297 A1 | 4/2003 | Chen et al. |
| 2003/0078172 A1 | 4/2003 | Guiramand et al. |
| 2003/0114520 A1 | 6/2003 | Pereira et al. |
| 2003/0118515 A1 | 6/2003 | Jew et al. |
| 2003/0130247 A1 | 7/2003 | Gans et al. |
| 2003/0175232 A1 | 9/2003 | Elliott et al. |
| 2003/0175315 A1 | 9/2003 | Yoo et al. |
| 2003/0180347 A1 | 9/2003 | Young et al. |
| 2003/0185839 A1 | 10/2003 | Podolsky |
| 2003/0194379 A1 | 10/2003 | Brugger et al. |
| 2003/0195128 A1 | 10/2003 | Deckman et al. |
| 2003/0206955 A1 | 11/2003 | Sonneville-Aubrun et al. |
| 2003/0215472 A1 | 11/2003 | Bonda et al. |
| 2004/0018228 A1 | 1/2004 | Fischell et al. |
| 2004/0028752 A1 | 2/2004 | Kamm et al. |
| 2004/0038912 A1 | 2/2004 | Michelet et al. |
| 2004/0053797 A1 | 3/2004 | Chen et al. |
| 2004/0058878 A1 | 3/2004 | Walker |
| 2004/0063787 A1 | 4/2004 | Villanueva |
| 2004/0067970 A1 | 4/2004 | Foster et al. |
| 2004/0072638 A1 | 4/2004 | Enos et al. |
| 2004/0076651 A1 | 4/2004 | Brocks et al. |
| 2004/0078896 A1 | 4/2004 | Hellyer et al. |
| 2004/0079361 A1 | 4/2004 | Clayton et al. |
| 2004/0105825 A1 | 6/2004 | Henning |
| 2004/0120917 A1 | 6/2004 | Perrier et al. |
| 2004/0127554 A1 | 7/2004 | Ghisalberti |
| 2004/0138179 A1 | 7/2004 | Goldstein et al. |
| 2004/0151671 A1 | 8/2004 | Abram et al. |
| 2004/0151756 A1 | 8/2004 | Richards et al. |
| 2004/0161447 A1 | 8/2004 | Paul |
| 2004/0184992 A1 | 9/2004 | Abram |
| 2004/0185123 A1 | 9/2004 | Mazzio et al. |
| 2004/0191196 A1 | 9/2004 | Tamarkin |
| 2004/0192754 A1 | 9/2004 | Shapira et al. |
| 2004/0195276 A1 | 10/2004 | Fuchs |
| 2004/0197276 A1 | 10/2004 | Takase et al. |
| 2004/0197295 A1 | 10/2004 | Riedel et al. |
| 2004/0219122 A1 | 11/2004 | Masuda et al. |
| 2004/0219176 A1 | 11/2004 | Dominguez |
| 2004/0220187 A1 | 11/2004 | Stephenson et al. |
| 2004/0229813 A1 | 11/2004 | DiPiano et al. |
| 2004/0234475 A1 | 11/2004 | Lannibois-Drean et al. |
| 2004/0241099 A1 | 12/2004 | Popp et al. |
| 2004/0247531 A1 | 12/2004 | Riedel et al. |
| 2004/0253275 A1 | 12/2004 | Eini et al. |
| 2004/0258627 A1 | 12/2004 | Riedel et al. |
| 2004/0265240 A1 | 12/2004 | Tamarkin et al. |
| 2005/0002976 A1 | 1/2005 | Wu |
| 2005/0013853 A1 | 1/2005 | Gil-Ad et al. |
| 2005/0031547 A1 | 2/2005 | Tamarkin et al. |
| 2005/0042182 A1 | 2/2005 | Arkin et al. |
| 2005/0054991 A1 | 3/2005 | Tobyn et al. |
| 2005/0069566 A1 | 3/2005 | Tamarkin et al. |
| 2005/0074414 A1 | 4/2005 | Tamarkin et al. |
| 2005/0075407 A1 | 4/2005 | Tamarkin et al. |
| 2005/0079139 A1 | 4/2005 | Jacques et al. |
| 2005/0084551 A1 | 4/2005 | Jensen et al. |
| 2005/0085843 A1 | 4/2005 | Opolski et al. |
| 2005/0101936 A1 | 5/2005 | Gonzales et al. |
| 2005/0106197 A1 | 5/2005 | Blin et al. |
| 2005/0123494 A1 | 6/2005 | Swaile et al. |
| 2005/0123496 A1 | 6/2005 | Shah et al. |
| 2005/0186142 A1 | 8/2005 | Tamarkin et al. |
| 2005/0186147 A1 | 8/2005 | Tamarkin et al. |
| 2005/0189377 A1 | 9/2005 | Lanzendorfer et al. |
| 2005/0196414 A1 | 9/2005 | Dake et al. |
| 2005/0205086 A1 | 9/2005 | Tamarkin et al. |
| 2005/0207837 A1 | 9/2005 | Kosh et al. |
| 2005/0222090 A1 | 10/2005 | Cheng et al. |
| 2005/0232869 A1 | 10/2005 | Tamarkin et al. |
| 2005/0244342 A1 | 11/2005 | Friedman et al. |
| 2005/0244354 A1 | 11/2005 | Speron |
| 2005/0245902 A1 | 11/2005 | Cornish et al. |
| 2005/0252995 A1 | 11/2005 | Westphal et al. |
| 2005/0255048 A1 | 11/2005 | Hirsh et al. |
| 2005/0258189 A1 | 11/2005 | Peterson et al. |
| 2005/0266035 A1 | 12/2005 | Healy et al. |
| 2005/0268416 A1 | 12/2005 | Sommers |
| 2005/0271596 A1 | 12/2005 | Friedman et al. |
| 2005/0271598 A1 | 12/2005 | Friedman et al. |
| 2005/0276836 A1 | 12/2005 | Wilson et al. |
| 2005/0281755 A1 | 12/2005 | Zarif et al. |
| 2005/0281766 A1 | 12/2005 | Martin et al. |
| 2005/0285912 A1 | 12/2005 | Delametter et al. |
| 2005/0287081 A1 | 12/2005 | Aust et al. |
| 2006/0008432 A1 | 1/2006 | Scarampi et al. |
| 2006/0018937 A1 | 1/2006 | Friedman et al. |
| 2006/0018938 A1 | 1/2006 | Neubourg |
| 2006/0029565 A1 | 2/2006 | Xu et al. |
| 2006/0051301 A1 | 3/2006 | Galopin et al. |
| 2006/0054634 A1 | 3/2006 | Mekata |
| 2006/0057168 A1 | 3/2006 | Larm et al. |
| 2006/0088561 A1 | 4/2006 | Eini et al. |
| 2006/0099151 A1 | 5/2006 | Neubourg |
| 2006/0108377 A1 | 5/2006 | Glynn et al. |
| 2006/0110418 A1 | 5/2006 | Johnson |
| 2006/0114745 A1 | 6/2006 | Ollmann et al. |
| 2006/0121073 A1 | 6/2006 | Goyal et al. |
| 2006/0140984 A1 * | 6/2006 | Tamarkin et al. ............. 424/400 |
| 2006/0140990 A1 | 6/2006 | Bortz et al. |
| 2006/0160713 A1 | 7/2006 | Sekine et al. |
| 2006/0165616 A1 | 7/2006 | Brock et al. |
| 2006/0177392 A1 | 8/2006 | Walden |
| 2006/0193789 A1 | 8/2006 | Tamarkin et al. |
| 2006/0193813 A1 | 8/2006 | Simonnet |

| | | | | | | |
|---|---|---|---|---|---|---|
| 2006/0204446 | A1 | 9/2006 | Lulla et al. | 2009/0291917 | A1 | 11/2009 | Akama et al. |
| 2006/0222675 | A1 | 10/2006 | Sabnis et al. | 2010/0111879 | A1 | 5/2010 | Tamarkin et al. |
| 2006/0233721 | A1 | 10/2006 | Tamarkin et al. | 2010/0221194 | A1 | 9/2010 | Loupenok |
| 2006/0239937 | A2 | 10/2006 | Neubourg | 2010/0266510 | A1* | 10/2010 | Tamarkin et al. ............... 424/43 |
| 2006/0251684 | A1 | 11/2006 | Annis et al. | 2011/0002857 | A1 | 1/2011 | Tamarkin et al. |
| 2006/0254597 | A1 | 11/2006 | Thompson | 2011/0002969 | A1 | 1/2011 | Serraima et al. |
| 2006/0263323 | A1 | 11/2006 | Hoang et al. | 2011/0212033 | A1 | 9/2011 | Tamarkin et al. |
| 2006/0269485 | A1 | 11/2006 | Friedman et al. | 2011/0268665 | A1 | 11/2011 | Tamarkin et al. |

FOREIGN PATENT DOCUMENTS

| | | |
|---|---|---|
| 2006/0272199 A1 12/2006 Licciardello et al. | | |
| 2006/0275218 A1 12/2006 Tamarkin et al. | CH | 639913 | 12/1983 |
| 2006/0275221 A1 12/2006 Tamarkin et al. | DE | 1 882 100 | 11/1963 |
| 2006/0285912 A1 12/2006 Eini et al. | DE | 1926796 | 11/1965 |
| 2006/0292080 A1 12/2006 Abram et al. | DE | 4140474 | 6/1993 |
| 2007/0009607 A1 1/2007 Jones | DE | 10009233 | 8/2000 |
| 2007/0017696 A1 1/2007 Lin et al. | DE | 10138495 | 2/2003 |
| 2007/0020213 A1 1/2007 Tamarkin et al. | DE | 102004016710 | 10/2005 |
| 2007/0020304 A1 1/2007 Tamarkin et al. | DE | 2 608 226 | 9/2007 |
| 2007/0027055 A1 2/2007 Koivisto et al. | EP | 0 156 507 | 10/1985 |
| 2007/0036831 A1 2/2007 Baker | EP | 0 186 453 | 7/1986 |
| 2007/0059253 A1 3/2007 Popp et al. | EP | 0 211 550 | 2/1987 |
| 2007/0069046 A1 3/2007 Eini et al. | EP | 0 214 865 | 3/1987 |
| 2007/0071688 A1 3/2007 Illel et al. | EP | 0 216 856 | 4/1987 |
| 2007/0098647 A1 5/2007 Neubourg | EP | 0 270 316 | 6/1988 |
| 2007/0134174 A1 6/2007 Irwin et al. | EP | 0 297 436 | 1/1989 |
| 2007/0140999 A1 6/2007 Puglia et al. | EP | 0 326 196 | 8/1989 |
| 2007/0142263 A1 6/2007 Stahl et al. | EP | 0 336 812 | 10/1989 |
| 2007/0148112 A1 6/2007 Dingley et al. | EP | 0 391 124 | 10/1990 |
| 2007/0148194 A1 6/2007 Amiji et al. | EP | 0 404 376 | 12/1990 |
| 2007/0154402 A1 7/2007 Trumbore et al. | EP | 0 414 920 | 3/1991 |
| 2007/0160548 A1 7/2007 Riccardi et al. | EP | 0 484 530 | 5/1992 |
| 2007/0224143 A1 9/2007 Konis | EP | 0 485 299 | 5/1992 |
| 2007/0237724 A1 10/2007 Abram et al. | EP | 0 488 089 | 6/1992 |
| 2007/0253911 A1 11/2007 Tamarkin et al. | EP | 0 504 301 | 9/1992 |
| 2007/0264317 A1 11/2007 Yosha et al. | EP | 0 528 190 | 2/1993 |
| 2007/0271235 A1 11/2007 Frank et al. | EP | 0 535 327 | 4/1993 |
| 2007/0280891 A1 12/2007 Tamarkin et al. | EP | 0 552 612 | 7/1993 |
| 2007/0281999 A1 12/2007 Fox et al. | EP | 0 569 773 | 11/1993 |
| 2007/0292355 A1* 12/2007 Tamarkin et al. ............... 424/43 | EP | 0 598 412 | 5/1994 |
| 2007/0292359 A1 12/2007 Friedman et al. | EP | 0 662 431 | 7/1995 |
| 2007/0292461 A1 12/2007 Tamarkin et al. | EP | 0 676 198 | 10/1995 |
| 2008/0008397 A1 1/2008 Kisilev | EP | 0 738 516 | 10/1996 |
| 2008/0015263 A1 1/2008 Bolotin et al. | EP | 0 757 959 | 2/1997 |
| 2008/0015271 A1 1/2008 Abram et al. | EP | 0 824 911 | 2/1998 |
| 2008/0031907 A1 2/2008 Tamarkin et al. | EP | 0 829 259 | 3/1998 |
| 2008/0031908 A1 2/2008 Aubrun-Sonneville et al. | EP | 0 928 608 | 7/1999 |
| 2008/0035155 A1 2/2008 Dahl | EP | 0 979 654 | 2/2000 |
| 2008/0044444 A1 2/2008 Tamarkin et al. | EP | 0 993 827 | 4/2000 |
| 2008/0058055 A1 3/2008 LeMay et al. | EP | 1 025 836 | 8/2000 |
| 2008/0063682 A1 3/2008 Cashman et al. | EP | 1 055 425 | 11/2000 |
| 2008/0069779 A1 3/2008 Tamarkin et al. | EP | 0 506 197 | 7/2001 |
| 2008/0131378 A1 6/2008 Keller et al. | EP | 1 215 258 | 6/2002 |
| 2008/0138293 A1* 6/2008 Tamarkin et al. ............... 424/45 | EP | 1 287 813 | 3/2003 |
| 2008/0138296 A1 6/2008 Tamarkin et al. | EP | 1 308 169 | 5/2003 |
| 2008/0152596 A1 6/2008 Friedman et al. | EP | 1 375 386 | 1/2004 |
| 2008/0153789 A1 6/2008 Dmowski et al. | EP | 1 428 521 | 6/2004 |
| 2008/0166303 A1 7/2008 Tamarkin et al. | EP | 1 438 946 | 7/2004 |
| 2008/0167376 A1 7/2008 Bar-Or et al. | EP | 1 189 579 | 9/2004 |
| 2008/0181854 A1 7/2008 Eini et al. | EP | 1 475 381 | 11/2004 |
| 2008/0188445 A1 8/2008 Muldoon et al. | EP | 1 483 001 | 12/2004 |
| 2008/0188446 A1 8/2008 Muldoon et al. | EP | 1 500 385 | 1/2005 |
| 2008/0193762 A1 8/2008 Dubertret et al. | EP | 1 537 916 | 6/2005 |
| 2008/0206155 A1 8/2008 Tamarkin et al. | EP | 1 600 185 | 11/2005 |
| 2008/0206159 A1 8/2008 Tamarkin et al. | EP | 1 734 927 | 12/2006 |
| 2008/0206161 A1 8/2008 Tamarkin et al. | EP | 1 758 547 | 3/2007 |
| 2008/0241079 A1 10/2008 Neubourg | EP | 1 584 324 | 11/2007 |
| 2008/0253973 A1 10/2008 Tamarkin et al. | EP | 1 889 609 | 2/2008 |
| 2008/0255498 A1 10/2008 Houle | FR | 2 591 331 | 6/1987 |
| 2008/0260655 A1 10/2008 Tamarkin et al. | FR | 2 640 942 | 6/1990 |
| 2008/0292560 A1 11/2008 Tamarkin et al. | FR | 2 736 824 | 1/1997 |
| 2008/0299220 A1 12/2008 Tamarkin et al. | FR | 2 774 595 | 8/1999 |
| 2008/0311167 A1 12/2008 Oronsky et al. | FR | 2 789 371 | 8/2000 |
| 2008/0317679 A1 12/2008 Tamarkin et al. | FR | 2 793 479 | 11/2000 |
| 2009/0041680 A1 2/2009 Tamarkin et al. | FR | 2 814 959 | 4/2002 |
| 2009/0068118 A1 3/2009 Eini et al. | FR | 2 833 246 | 6/2003 |
| 2009/0093514 A1 4/2009 Statham et al. | FR | 2 840 903 | 12/2003 |
| 2009/0130029 A1 5/2009 Tamarkin et al. | FR | 2 843 373 | 2/2004 |
| 2009/0131488 A1 5/2009 Harel et al. | FR | 2 845 672 | 4/2004 |
| 2009/0175799 A1 7/2009 Tamarkin et al. | FR | 2 848 998 | 6/2004 |
| 2009/0180970 A1 7/2009 Tamarkin et al. | | | |

| | | | | | | |
|---|---|---|---|---|---|---|
| FR | 2 860 976 | 4/2005 | | JP | 2002/012513 | 1/2002 |
| FR | 2 915 891 | 11/2008 | | JP | 2002/047136 | 2/2002 |
| GB | 808 104 | 1/1959 | | JP | 2002/524490 | 8/2002 |
| GB | 808 105 | 1/1959 | | JP | 2002/302419 | 10/2002 |
| GB | 922 930 | 4/1963 | | JP | 2003/012511 | 1/2003 |
| GB | 933 486 | 8/1963 | | JP | 2003/055146 | 2/2003 |
| GB | 998 490 | 7/1965 | | JP | 2004/047136 | 2/2004 |
| GB | 1 026 831 | 4/1966 | | JP | 2004/250435 | 9/2004 |
| GB | 1 033 299 | 6/1966 | | JP | 2004/348277 | 12/2004 |
| GB | 1 081 949 | 9/1967 | | JP | 2005/314323 | 11/2005 |
| GB | 1 121 358 | 7/1968 | | JP | 2005/350378 | 12/2005 |
| GB | 1 162 684 | 8/1969 | | JP | 2006/008574 | 1/2006 |
| GB | 1 170 152 | 11/1969 | | JP | 2006/036317 | 2/2006 |
| GB | 1 201 918 | 8/1970 | | JP | 2006/103799 | 4/2006 |
| GB | 1 347 950 | 2/1974 | | JP | 2006525145 | 11/2006 |
| GB | 1 351 761 | 5/1974 | | JP | 2007/131539 | 5/2007 |
| GB | 1 351 762 | 5/1974 | | JP | 2007326996 | 12/2007 |
| GB | 1 353 381 | 5/1974 | | KR | 143232 | 7/1998 |
| GB | 1 376 649 | 12/1974 | | KR | 2001/003063 | 1/2001 |
| GB | 1 397 285 | 6/1975 | | RU | 2277501 | 6/2006 |
| GB | 1 408 036 | 10/1975 | | UA | 66796 | 6/2004 |
| GB | 1 457 671 | 12/1976 | | WO | 82/01821 | 6/1982 |
| GB | 1 489 672 | 10/1977 | | WO | 86/05389 | 9/1986 |
| GB | 2 004 746 | 4/1979 | | WO | 88/01502 | 3/1988 |
| GB | 1 561 423 | 2/1980 | | WO | 88/01863 | 3/1988 |
| GB | 2 114 580 | 8/1983 | | WO | 88/08316 | 11/1988 |
| GB | 2 153 686 | 8/1985 | | WO | 89/06537 | 7/1989 |
| GB | 2 172 298 | 9/1986 | | WO | 90/05774 | 5/1990 |
| GB | 2 206 099 | 12/1988 | | WO | 91/11991 | 8/1991 |
| GB | 2 166 651 | 5/1996 | | WO | 92/00077 | 1/1992 |
| GB | 2 337 461 | 11/1999 | | WO | 92/05142 | 4/1992 |
| GB | 2 367 809 | 4/2002 | | WO | 92/05763 | 4/1992 |
| GB | 2 406 330 | 3/2005 | | WO | 92/11839 | 7/1992 |
| GB | 2 406 791 | 4/2005 | | WO | 93/25189 | 12/1993 |
| IL | 49491 | 9/1979 | | WO | 94/06440 | 3/1994 |
| IL | 152 486 | 5/2003 | | WO | 96/03115 | 2/1996 |
| JP | 60001113 | 4/1978 | | WO | 96/19921 | 7/1996 |
| JP | 55069682 | 5/1980 | | WO | 96/24325 | 8/1996 |
| JP | 57044429 | 3/1982 | | WO | 96/26711 | 9/1996 |
| JP | 56039815 | 4/1984 | | WO | 96/27376 | 9/1996 |
| JP | 61275395 | 12/1986 | | WO | 96/39119 | 12/1996 |
| JP | 62241701 | 10/1987 | | WO | 97/03638 | 2/1997 |
| JP | 63119420 | 5/1988 | | WO | 97/39745 | 10/1997 |
| JP | 1100111 | 4/1989 | | WO | 98/17282 | 4/1998 |
| JP | 1156906 | 6/1989 | | WO | 98/18472 | 5/1998 |
| JP | 2184614 | 7/1990 | | WO | 98/19654 | 5/1998 |
| JP | 2255890 | 10/1990 | | WO | 98/21955 | 5/1998 |
| JP | 4282311 | 10/1992 | | WO | 98/23291 | 6/1998 |
| JP | 4312521 | 11/1992 | | WO | 98/36733 | 8/1998 |
| JP | 5070340 | 3/1993 | | WO | 98/52536 | 11/1998 |
| JP | 5213734 | 8/1993 | | WO | 99/08649 | 2/1999 |
| JP | 6100414 | 4/1994 | | WO | 99/20250 | 4/1999 |
| JP | H06-263630 | 6/1994 | | WO | 99/37282 | 7/1999 |
| JP | 6329532 | 11/1994 | | WO | 99/53923 | 10/1999 |
| JP | 2007/155667 | 6/1995 | | WO | 00/09082 | 2/2000 |
| JP | 7215835 | 8/1995 | | WO | 00/15193 | 3/2000 |
| JP | 2008/040899 | 2/1996 | | WO | 00/23051 | 4/2000 |
| JP | 8501529 | 2/1996 | | WO | 00/33825 | 6/2000 |
| JP | 8119831 | 5/1996 | | WO | 00/38731 | 7/2000 |
| JP | 8165218 | 6/1996 | | WO | 00/61076 | 10/2000 |
| JP | 8277209 | 10/1996 | | WO | 00/76461 | 12/2000 |
| JP | 09 084855 | 3/1997 | | WO | 01/05366 | 1/2001 |
| JP | 9099553 | 4/1997 | | WO | 01/08681 | 2/2001 |
| JP | 9110636 | 4/1997 | | WO | 01/10961 | 2/2001 |
| JP | 10114619 | 5/1998 | | WO | 01/53198 | 7/2001 |
| JP | 3050289 | 9/1998 | | WO | 01/54212 | 7/2001 |
| JP | 2010/332456 | 12/1998 | | WO | 01/54679 | 8/2001 |
| JP | 11501045 | 1/1999 | | WO | 01/62209 | 8/2001 |
| JP | 11250543 | 9/1999 | | WO | 01/70242 | 9/2001 |
| JP | 2000/017174 | 1/2000 | | WO | 01/82880 | 11/2001 |
| JP | 2000/080017 | 3/2000 | | WO | 01/82890 | 11/2001 |
| JP | 2000/128734 | 5/2000 | | WO | 01/85102 | 11/2001 |
| JP | 2000/191429 | 7/2000 | | WO | 01/85128 | 11/2001 |
| JP | 2000/239140 | 9/2000 | | WO | 01/95728 | 12/2001 |
| JP | 2000/351726 | 12/2000 | | WO | 02/00820 | 1/2002 |
| JP | 2000/354623 | 12/2000 | | WO | 02/15860 | 2/2002 |
| JP | 2001/002526 | 1/2001 | | WO | 02/15873 | 2/2002 |
| JP | 2001/019606 | 1/2001 | | WO | 02/28435 | 4/2002 |
| JP | 2001/072963 | 3/2001 | | WO | 02/41847 | 5/2002 |

| | | |
|---|---|---|
| WO | 02/43490 | 6/2002 |
| WO | 02/062324 | 8/2002 |
| WO | 02/078667 | 10/2002 |
| WO | 02/087519 | 11/2002 |
| WO | 03/000223 | 1/2003 |
| WO | 03/002082 | 1/2003 |
| WO | 03/013984 | 2/2003 |
| WO | 03/051294 | 6/2003 |
| WO | 03/053292 | 7/2003 |
| WO | 03/055445 | 7/2003 |
| WO | 03/055454 | 7/2003 |
| WO | 03/070301 | 8/2003 |
| WO | 03/071995 | 9/2003 |
| WO | 03/075851 | 9/2003 |
| WO | 03/092641 | 11/2003 |
| WO | 03/097002 | 11/2003 |
| WO | 2004/017962 | 3/2004 |
| WO | 2004/037197 | 5/2004 |
| WO | 2004/037225 | 5/2004 |
| WO | 2004/003284 | 8/2004 |
| WO | 2004/064769 | 8/2004 |
| WO | 2004/064833 | 8/2004 |
| WO | 2004/071479 | 8/2004 |
| WO | 2004/078158 | 9/2004 |
| WO | 2004/078896 | 9/2004 |
| WO | 2004/093895 | 11/2004 |
| WO | 2004/112780 | 12/2004 |
| WO | 2005/011567 | 2/2005 |
| WO | 2005/018530 | 3/2005 |
| WO | 2005/032522 | 4/2005 |
| WO | 2005/044219 | 5/2005 |
| WO | 2005/063224 | 7/2005 |
| WO | 2005/065652 | 7/2005 |
| WO | 2005/076697 | 8/2005 |
| WO | 2005/097068 | 10/2005 |
| WO | 2005/102282 | 11/2005 |
| WO | 2005/102539 | 11/2005 |
| WO | 2005/117813 | 12/2005 |
| WO | 2006/003481 | 1/2006 |
| WO | 2006/010589 | 2/2006 |
| WO | 2006/011046 | 2/2006 |
| WO | 2006/020682 | 2/2006 |
| WO | 2006/028339 | 3/2006 |
| WO | 2006/031271 | 3/2006 |
| WO | 2006/045170 | 5/2006 |
| WO | 2006/079632 | 8/2006 |
| WO | 2006/081327 | 8/2006 |
| WO | 2006/091229 | 8/2006 |
| WO | 2006/100485 | 9/2006 |
| WO | 2006/120682 | 11/2006 |
| WO | 2006/121610 | 11/2006 |
| WO | 2006/122158 | 11/2006 |
| WO | 2006/129161 | 12/2006 |
| WO | 2006/131784 | 12/2006 |
| WO | 2007/007208 | 1/2007 |
| WO | 2007/012977 | 2/2007 |
| WO | 2007/023396 | 3/2007 |
| WO | 2007/031621 | 3/2007 |
| WO | 2007/039825 | 4/2007 |
| WO | 2007/050543 | 5/2007 |
| WO | 2007/054818 | 5/2007 |
| WO | 2007/072216 | 6/2007 |
| WO | 2007/085899 | 8/2007 |
| WO | 2007/085902 | 8/2007 |
| WO | 2007/099396 | 9/2007 |
| WO | 2007/111962 | 10/2007 |
| WO | 2008/008397 | 1/2008 |
| WO | 2008/010963 | 1/2008 |
| WO | 2008/038147 | 4/2008 |
| WO | 2008/041045 | 4/2008 |
| WO | 2008/075207 | 6/2008 |
| WO | 2008/087148 | 7/2008 |
| WO | 2008/110872 | 9/2008 |
| WO | 2008/152444 | 12/2008 |
| WO | 2009/007785 | 1/2009 |
| WO | 2009/069006 | 6/2009 |
| WO | 2009/072007 | 6/2009 |
| WO | 2009/087578 | 7/2009 |
| WO | 2009/090495 | 7/2009 |
| WO | 2009/090558 | 7/2009 |
| WO | 2009/098595 | 8/2009 |
| WO | 2011/039637 | 4/2011 |
| WO | 2011/039638 | 4/2011 |

OTHER PUBLICATIONS

U.S. Appl. No. 60/815,948, filed Jun. 23, 2006, Tamarkin.
U.S. Appl. No. 60/818,634, filed Jul. 5, 2006, Friedman.
U.S. Appl. No. 60/843,140, filed Sep. 8, 2006, Tamarkin.
U.S. Appl. No. 61/248,144, filed Oct. 2, 2009, Tamarkin.
U.S. Appl. No. 61/322,148, filed Apr. 8, 2010, Tamarkin.
U.S. Appl. No. 61/363,577, filed Jul. 12, 2010, Eini.
"HLB Systems", http://pharmcal.tripod.com/ch17.htm, Accessed Sep. 17, 2010, pp. 1-3.
'Surfactant' [online]. Wikipedia, 2010, [retrieved on Oct. 24, 2010]. Retrieved from the Internet: <URL: http://en.wikipedia.org/wiki/Surfactant>, 7 pages.
Adachi, Shuji. "Storage and Oxidative Stability of O/W/ Nano-emulsions." Foods Food Ingredients. J. Jpn. vol. 209, No. 11. 2004. 1 page.
Alcohol SDA 40B.http://www.pharmco-prod.com/pages/MSDS/SDA.sub.--40B.sub.--200.pdf Accessed Dec. 9, 2008, 2 pages.
Ambrose, Ursula et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds," Antimicrobial Agents and Chemotherapy, vol. 35, No. 9, pp. 1799-1803, 1991.
Anton, N. et al. "Water-in-Oil Nano-Emulsion Formation by the phase inversion Temperature Method: A Novel and General Concept, a New Template for Nanoencapsulation," *Proceedings of the 33rd Annual Meeting and Exposition of the Controlled Release Society*, Jul. 2006, Vienna, Austria, 2 pages.
Arct et al., "Common Cosmetic Hydrophilic Ingredients as Penetration Modifiers of Flavonoids", International Journal of Cosmetic Science, 24(6):357-366 (2002)—Abstract, 1 page.
Arisan, http://www.arisankimya.com/kozmetik.htm Accessed Dec. 10, 2008, 8 pages.
Augsburger, Larry L. et al. "Bubble Size Analysis of High Consistency Aerosol Foams and Its Relationship to Foam Rheology. Effects of Container Emptying, Propellent Type, and Time." Journal of Pharmaceutical Sciences. vol. 57, No. 4. Apr. 1968. pp. 624-631.
Austria, et al., "Stability of Vitamin C Derivatives in Solution and Topical Formulations", Journal of Pharmaceutical and Biomedical Analysis, 15:795-801 (1997).
Barry, B.W. et al, Comparative bio-availability and activity of proprietary topical corticosteroid preparations: vasoconstrictor assays on thirty-one ointments, British Journal of Dermatology, 93, 563-571, 1975.
Benet, et al., Application of NMR for the Determination of HLB Values of Nonionic Surfactants, Journal of the American Oil Chemists Society, vol. 49, 1972, 499-500.
Bernstein, et al., Effects of the Immunomodulating Agent R837 on Acute and Latent Herpes Simplex Virus Type 2 Invections, Antimicrobial Agents and Chemotherapy, 33(9):1511-1515 (1989).
Blute, "Phase behavior of alkyl glycerol ether surfacants", Physical Chemistry Tenside Sur. Det., 35(3):207-212 (1998).
Brenes, et al., "Stability of Copigmented Anthocyanins and Asorbics Acid in a Grape Juice Model System", J. Agric Food Chem, 53(1):49-56 (2005)—Abstrace, 1 page.
Bronopol. Revtrieved online on Jun. 4, 2011. <URL:http://chemicalland21.com/specialtychem/perchem/BRONOPOL.html>. Jul. 17, 2006. 4 pages.
Buck, et al., "Treatment of Vaginal Intraephithelial Neoplasia (Primarily Low Grade) with Imiquimod 5% Cream", Journal of Lower Genetial Tract Disease, 7(3):290-293 (2003).
Bucks, Daniel A.W., et al., "Bioavailability of Topically Administered Steroids: A 'Mass Balance' Technique," Journal of Investigative Dermatology, vol. 91, No. 1, Jul. 1988, pp. 29-33.
Bunker,et al., "Alterations in Scalp Blood Flow after the Epicutaneous Application of 3% Minoxidil and 0.1% Hexyl Nicotinate in Alopecia", Presented as a poster at the meeting of the British Society for Investigavie Dermatology, York, Sep. 1986 (2 pages).
Burton, et al., "Hypertrichosis Due to Minoxidil", British Journal of Dermatology, 101:593-595 (1979).

Campos, et al., "Ascorbic Acid and Its Derivatives in Cosmetic Formulations", Cosmetics and Toiletries, 115(6):59-62 (2000)—Abstract, 1 page.
Carbowax 1000MSDS; http://www.sciencelab.com/xMSDS-Polyethylene.sub.--glycol.sub.--1000-9926-622. Accessed Dec. 13, 2008, 6 pages.
Carelli, et al., "Effect of Vehicles on Yohimbine Permeation Across Excised Hairless Mouse Skin", Pharm Acta Helv, 73(3):127-134 (1998)—Abstract, 1 page.
Chebil, et al., "Soulbility of Flavonoids in Organic Solvents", J. Chem. Eng. Data, 52(5):1552-1556 (2007)—Abstract, 1 page.
Chevrant-Breton, et al., "Etude du Traitement Capillaire <<Bioscalin>> dans les Alopecies Diffuses de la Femme", Gazette Medicale, 93(17):75-79 (1986) [English abstract].
Chiang, et al., "Bioavailability Assessment of Topical Delivery Systems: In Vitro Delivery of Minoxidil from Prototypical Semi-Solid Formulations", Int. J. Pharm, 49(2):109-114 (1989)—Abstract, 1 page.
Chinnian, et al., "Photostability Profiles of Minoxidil Solutions", PDA J. Pharm Sci Technol., 50(2):94-98 (1996)—Abstract, 1 page.
Chollet, et al., "Development of a Topically Active Imiquimod Formulation", Pharmaceutical Development and Technology, 4(1):35-43 (1999).
Chollet, et al., "The Effect of Temperatures on the Solubility of Immiquimod in Isostearic Acid", Abstract 3031, Pharmaceutical Research, vol. 14, No. 11 Supplemental (November), p. S475 (1997), 2 pages.
Coetzee, "Acceptability and Feasibility of Micralax applicators and of methyl cellulose gel placebo for large-scale clinical trials of vaginal microbicides," Nicol.AIDS 2001, vol. 15, No. 14, pp. 1837-1842.
Colloidal Silica. Retrieved online on Jun. 4, 2011. <URL:http://www.grace.com/engineeredmaterials/materialsciences/colloidalsilica/default.aspx>. Copyright 2011. 4 pages.
Croda 2. Croda Cetomacrogol 1000 Product Information Sheet. 2011 (no month given). 1 page.
Croda. Aracel 165 Product Summary. 2011 (no month given). 1 page.
D.W.A. Sharp Dictionary of Chemistry, Penguin Books, 1983, 3 pages.
Dalby, "Determination of Drug Solubility in Aerosol Propellants," Pharmaceutical Research, vol. 8, No. 9, 1991, pp. 1206-1209.
Dawber, et al., "Hypertrichosis in Females Applying Minoxidil Topical Solution and in Normal Controls", JEADV, 17:271-275 (2003).
Denatonium Benzoate http://www.newdruginfo.com/pharmaceopeia/usp28/v28230/usp28nf23s0.sub.--m- 22790.htm Accessed Dec. 9, 2008, 2 pages.
Dentinger, et al., "Stability of Nifedipine in an Extemporaneously Compounded Oral Solution", American Journal of Health-System Pharmacy, 60(10):1019-1022 (2003)—Abstract, 1 page.
Draelos, Z. D. "Antiperspirants and the Hyperhidrosis Patients." Dermatologic Therapy. 2001. vol. 14. pp. 220-224.
Edens, et al., "Storage Stability and Safey of Active Vitamin C in a New Dual-Chamber Dispenser", Journal of Applied Cosmetology, 17(4):136-143 (1999)—Abstract, 1 page.
Edirisinghe, et al., "Effect of fatty acids on endothelium-dependent relaxation in the rabbit aorta", Clin Sci (Load). Aug. 2006; 111(2): 145-51.
Edwards, "Imiquimod in Clinical Practice", J. Am Acad Dermatol., 43(1, Pt 2):S12-S17 (2000)—Abstract, 1 page.
Emulsifiers with HLB values. http://www.theherbarie.com/files/resources-center/formulating/Emulsifiers-.sub.--HLB.sub.--Values.pdf accessed Aug. 5, 2009 (3 pps).
Encyclopedia of Pharmaceutical Technology, Second Edition, vol. 3, Copyright 2002, 4 pages.
Esposito, E. et al. "Nanosystems for Skin Hydration: A Comparative Study." International Journal of Cosmetic Science. 29. 2007. pp. 39-47.
Ethanol, Accessed http://www.sigmaaldrich.com/catalog/ProductDetail.do?N4=E7023SIAL&N5=SEAR- CH.sub.--CONCAT.sub.--PNOBBRAND.sub.--KEY&F=SPEC Dec. 9, 2008, 2 pages.
Ethylene Oxide Derivatives: An Essence of Every Industry. A definition of Emulsifier. Http://www.emulsifiers.in/ethylene_oxide_derivatives2.htm. Accessed Jul. 12, 2011. 3 pages.
Farahmand, et al., "Formulation and Evaluation of a Vitamin C Multiple Emulsion", Pharmaceutical Development and Technology, 11(2):255-261 (2006)—Abstract, 1 page.
Final Office Action for U.S. Appl. No. 11/430,437, Tamarkin et al., Dec. 16, 2008, 24 pages.
Flick, Cosmetic and Toiletry Formulations, vol. 5, 2nd Edition, Copyright 1996, 63 pages. Relevant pp. 251-309.
Fontana, Anthony J., "Water Activity: Why It is Important for Food Safety," International Conference on Food Safety, Nov. 16-18, 1998, pp. 177-185.
Gallarate, et al., "On the Stability of Ascorbic Acid in Emulsified Systems for Topical and Cosmetic Use", International Journal of Pharmaceutics, 188:233-241 (1999).
Galligan, John et al., "Adhesive Polyurethane Liners for Anterior Restorations," J. Dent. Res., Jul.-Aug. 1968, pp. 629-632.
Gelbard et al. "Primary Pediatric Hyperhidrosis: A Review of Current Treatment Options." Pediatric Dermatology. 2008. 25 (6). pp. 591-598.
Graves, S. et al. "Structure of Concentrated Nanoemulsions." The Journal of Chemical Physics.. 122 America Institute of Physics. Published Apr. 1, 2005. 6 pages.
Hall, Karla, "Diaper Area Hemangiomas: A Unique Set of Concerns," http://members.tripod.com/.about.Michelle.sub.--G/diaper.html, Dec. 1, 2008, 8 pages.
Hallstar. Retrieved online on Jun. 4, 2011. <URL:http://www.hallstar.com/pis.php?product=1H022>. 1 page.
Harrison, et al., "Effects of cytokines and R-837, a cytokine inducer, on UV-irradiation augmented recurrent genital herpes in guinea pigs", Antivial Res., 15(4):315-322 (1991).
Harrison, et al., "Modification of Immunological Responses and Clinical Disease During Topical R-837 Treatment of Genital HSV-2 Infection", Antiviral Research, 10:209-224 (1988).
Harrison, et al., "Pharmacokinetics and Safety of Iminquimod 5% Cream in the Treatment of Actinic Keratoses of the Face, Scalp, or Hands and Arms", Arch. Dermatol. Res., 296(1):6-11 (2004)—Abstract, 1 page.
Hashim, et al. "Tinea versicolor and visceral leishmaniasis," Int J Dermatol., Apr. 1994; 33(4), pp. 258-259 (abstract only).
Heart Failure, The Merck Manual, 2008 <<http://www.merck.com/mmhe/sec03/ch025/ch025a.html>> 12 pages.
Hepburn, NC., "Cutaneous leishmaniasis," Clin Exp Dermatol, Jul. 2000; 25(5), pp. 363-370 (abstract only).
Hill, Randall M. (Ed.) Silicone Surfactants, Table of Contents and Chapter 7, "Silicone Surfactants: Applicants in the Personal Care Industry," by David T. Floyd, 1999 (30 Pages).
http://ibabydoc.com/online/diseaseeczema.asp., Atopic Dermatitis, Copyright 2000, 6 pages.
http://web.archive.org/web/20000106225413/http://pharmacy.wilkes.edu/kibbeweb/lab7.html, Characteristics of Surfactants and Emulsions, Jan. 29, 2010, 5 pages.
http://www.agworkshop.com/p3.asp, AG&Co. Essential oil workshop. 1 page. Accessed Jan. 31, 2010.
Hubbe, Martin. Mini-Encyclopedia of Papermaking Wet-End Chemistry: Additives and Ingredients, their Composition, Functions, Strategies for Use. Retrieved online on Jun. 4, 2011. <URL://http://www4.ncsu.edu/~hubbe/CSIL.htm>. Feb. 1, 2001. 2 pages.
ICI Americas Inc. "The HLB System: A Time-Saving Guide to Emulsifier Selection." Mar. 1980. pp. 1-22.
Ikuta, et al., "Scanning Electron Microscopic Observation of Oil/Wax/Water/Surfacant System", Journal of SCCJ, 34(4):280-291 (2004)—Abstract, 1 page.
Indomethacin. Retrieved online on Jun. 3, 2011. <URL:http://it03.net/com/oxymatrine/down/1249534834.pdf>. Aug. 15, 2009. 3 pages.
Innocenzi, Daniele et al., "An Open-Label Tolerability and Effacy Study of an Aluminum Sesquichlorhydrate Topical Foam in Axillary and Palmar Primary Hyperhidrosis," Dermatologic Therapy, vol. 21, S27-S30, 2008.
Izquierdo, P. et al. "Formation and Stability of Nano-Emulsions Prepared Using the Phase Inversion Temperature Method." University of Barcelona. Sep. 17, 2001. 1 page.
Kalkan, et al., The Measurement of Sweat Intensity Using a New Technique, Tr. J. of Medical Sciences 28, 515-517 (1998).

Kanamoto, et al., "Pharmacokinetics of two rectal dosage forms of ketoprofen in patients after anal surgery," J Pharmacobiodyn., Mar. 1988; 11(3):141-5.
Kang,et al., "Enhancement of the Stability and Skin Penetration of Vitamin C by Polyphenol", Immune Netw., 4(4):250-254 (2004)—Abstract, 1 page.
Kathon.TM. CG (product information sheet by Rohm and Haas, Jun. 2006).
Kim, "Stability of Minoxidil in Aqueous Solution", Yakhak Hoechi, 30(5):228-231 (1986)—Abstract, 1 page.
Kinnunen, "Skin reactions to hexylene glycol," Contact Dermatitis Sep. 1989; 21(3): 154-8.
Kleber, M.D., H.D. et al., "Treatment of Patients with Substance Use Disorders, Second Edition," pp. 1-276, 2006.
Kreuter, J. "Nanoparticles and microparticles for drug and vaccine delivery," J. Anat. (1996) 189, pp. 503-505.
Kumar, J. et ak., "Application of Broad Spectrum Antiseptic Povidone Iodine as Powerful Action: A Review," Journal of Pharmaceutical Science and Technology vol. 1(2), 2009, 48-58.
Kwak et al. "Study of Complete Transparent Nano-Emulsions which Contain Oils." IFSCC Conference 2003, Seoul, Korea, Sep. 22-24, 2003. 3 pages.
Lautenschlager, Dr. Hans. "A Closer Look on Natural Agents: Facts and Future Aspects." Kosmetic Konzept. Kosmetische Praxis. 2006 (no month given). (5), 8-10. 3 pages.
Lebwohl et al. "Treatment of Psoriasis. Part 1. Topical Therapy and Phototherapy." *J. Am. Acad. Dermatol*. 45:487-498. Oct. 2001.
Lee, et al., "The Stabilization of L-Ascorbic Acid in Aqueous Solution and Water-in-Oil-in-Water Double Emulsion by Controlling pH and Electrolyte Concentration", J. Cosmet. Sci., 55:1-12 (Jan./Feb. 2004).
Leung, et al., "Bioadhesive Drug Delivery in Water-Soluble Polymers," American Chemical Society, Chapter 23, 1991, pp. 350-366.
Licking Vaginal Dryness without a Prescription. Accessed http://www.estronaut.com/a/vag.sub.--dryness.htm on Dec. 14, 2008, 3 pages.
Lippacher, A. et al. "Liquid and Semisolid SLN Dispersions for Topical Application" Rheological Characterization. European Journal of Pharmaceutics and Biopharmaceutics. 58. 2004. pp. 561-567.
Lupo, "Antioxidants and Vitamins in Cosmetics", Clinics in Dermatology, 19:467-473 (2001).
Martindale, The extra pharmacopoeia [28th] edition, Eds.: Reynolds, J.E.F. and Prasad, A.B., The Pharmaceutical Press, London, pp. 862-864, 1982.
Material Safety Data Sheet, Science Lab.com, Polyethylene Glycol 1000, MSDS, Nov. 6, 2008, 6 pages.
Merck Index, An Encyclopedia of Chemicals, Drugs, and Biologicals. $13^{th}$ Edition. O'Neil et al eds. Entries 1058, 2350, 6143, and 8803. 2001. 7 pages.
Merck Manual Home Edition. "Excessive Sweating: Sweating Disorders." Accessed Apr. 14, 2011 at www.merckmanuals.com/home/print/sec18/ch206/ch206c.html. 2 pages.
Messenger, et al., "Minoxidil: Mechanisms of Action on Hair Growth", British Journal of Dermatology, 150:186-194 (2004).
Metz, et al., "A Phase I Study of Topical Tempol for the Prevention of Alopecia Induced by Whole Brain Radiotherapy", Clinical Cancer Research, 10:6411-6417 (2004).
Meucci, et al., "Ascorbic Acid Stability in Aqueous Solutions", Acta Vitaminol Enzymol, 7(3-4):147-153 (1985)—Abstract, 1 page.
MMP Inc. International Development and Manufacturing, "Formulating specialities," http://mmpinc.com, 3 pages. Feb. 2, 2010.
Molan, Peter Clark, "World Wide Wounds," Dec. 2001, 13 pages.
Morgan, Timothy M., et al., "Enhanced Skin Permeation of Sex Hormones with Novel Topical Spray Vehicles," Journal of Pharmaceutical Sciences, vol. 87, No. 10, Oct. 1998, pp. 1213-1218.
No Author Listed. "Opitmization of Nano-Emulsions Production by Microfluidization." European Food Research and Technology. vol. 225, No. 5-6. Sep. 2007. Abstract. 1 page.
Office Action for U.S. Appl. No. 11/430,437, Tamarkin et al., May 9, 2008, 27 pages.
Office Action received from the U.S. Patent Office, U.S. Appl. No. 11/430,599, Jul. 28, 2008 (59 pages).
Pendergrass, "The shape and dimension of the human vagina as seen in three-dimensional vinyl polysiloxane casts," Gynecol Obstet. Invest. 1996:42(3):178-82.
Prescription Information for Aldara, Mar. 2007 (29 pages).
Prevent. (2007). In the American Heritage Dictionary of the English Language. Retrieved from http://www.credoreference.com/entry/hmdictenglang/prevent. 1 page.
Psoriasis, http://www.quickcare.org/skin/causes-of0psoriasis.html. Accessed Sep. 9, 2010—3 pages.
Purcell, Hal C. "Natural Jojoba Oil Versus Dryness and Free Radicals." Cosmetics and Toiletries Manufacture Worldwide. 1988. 4 pages.
Raschke, et al., "Topical Activity of Ascorbic Acid: From In Vitro Optimization to In Vivo Efficacy", Skin Pharmacology and Physiology, 17(4):200-206 (2004)—Abstract, 1 page.
Receptacle. Merriam Webster. Http://www.merriam-webster.com/dictionary/receptacle. Accessed Jul. 12, 2011. 1 page.
Richwald, "Imiquimod", Drugs Today, 35(7):497 (1999)—Abstract, 1 page.
Rieger and Rhein. "Emulsifier Selection/HLB." Surfactants in Cosmetics. 1997 (no month given). 1 page.
Savin, et al., "Tinea versicolor treated with terbinafine 1% solution," Int J. Dermatol, Nov. 1999; 38(11), pp. 863-865.
Schulze, M.D., Harry "Iodine and Sodium Hypochlorite as Wound Disinfectants," The British Medical Journal, pp. 921-922, 1915.
Scientific Discussion for the approval of Aldara, EMEA 2005 (10 pages).
Scott as Published in Pharmaceutical Dosage Forms; Disperse Systems, vol. 3, Copyright 1998, 120 pages.
Seborrheic Dermatitis, http://www.cumc.columbia.edu/student/health/pdf/R-S/Seborrhea%20Dermatitis.pdf. Access Sep. 9, 2010, 2 pages.
Shear, et al., "Pharmacoeconomic analysis of topical treatments for tinea infections," Pharmacoeconomics. Mar. 1995; 7(3); pp. 251-267 (abstract only).
Sheu, et al., "Effect of Tocopheryl Polyethylene Glycol Succinate on the Percutaneous Penetration of Minoxidil from Water/Ethanol/Polyethylene Glycol 400 Solutions", Drug Dev. Ind. Pharm., 32(5):595-607 (2006)—Abstract, 1 page.
Shim, et al., "Transdermal Delivery of Mixnoxidil with Block Copolymer Nanoparticles", J. Control Release, 97(3):477-484 (2004)—Abstract, 1 page.
Sigma Aldrich, "HLB-Numbers in Lithography Nanopatterning," http://www.sigmaaldrich.com/materials-science/micro-and-nanoelectronics/1-ithography-nanopatterning/hlb-numbers.html, accessed: Feb. 2, 2009, pp. 1-3.
Silicone. Definition. Retrieved Apr. 19, 2011 from http://www.oxforddictionaries.com/definition/silicone?view=uk. 1 page.
Simovic, S. et al., "The influence of Processing Variables on Performance of O/W Emulsion Gels Based on Polymeric Emulsifier (Pemulen ÓTR-2NF)," International Journal of Cosmetic Science, vol. 2(2): abstract only. Dec. 24, 2001, 1 page.
Skin Biology, CP Serum—Copper-Peptide Serum for Skin Regeneration and Reducing Wrinkles, Skin Biology, http;//web.archive.org/web/20030810230608/http://www.skinbio.com/cpserum.-html, Dec. 1, 2008, 21 pages.
Skin Deep Cosmetics. PPG-40-PEG-60 Lanolin Oil http://www.cosmeticsdatabase.com/ingredient/722972/PPG-40-PEG-60_Lanolin_Oil/?ingred06=722972. 2010, 3 pages.
Sonneville-Aubrun, O. et al. "Nanoemulsions: A New Vehicle for Skincare Products." Advances in Colloid and Interface Science. 108-109.. 2004. pp. 145-149.
Squire. J, "A randomised, single-blind, single-centre clinical trial to evaluate comparative clinical efficacy of shampoos containing ciclopirox olamine (1.5%) and salicylic acid (3%), or ketoconazole (2%, Nizoral) for the treatment of dandruff/seborrhoeic dermatitis," Dermatolog Treat. Jun. 2002;13(2):51-60 (abstract only).
Sreenivasa, et al., "Preparation and Evaluation of Minoxidil Gels for Topical Application in Alopecia", Indian Journal of Pharmaceutical Sciences, 68(4):432-436 (2006), 11 pages.

Sugisaka, et al., "The Physiochemical Properties of Imiquimod, the First Imidazoquinoline Immune Response Modifier", Abstract 3030, Pharmaceutical Research, vol. 14, No. 11 Supplemental (November), p. S475 (1997), 2 pages.

Tan et al., "Effect of Carbopol and Polyvinlpyrrolidone on the Mechanical Rheological and Release Properties of Bioadhesive Polyethylene Glycol Gels," AAPS PharmSciTech, 2000; 1(3) Article 24, 2000, 10 pages.

Tanhehco, "Potassium Channel Modulators as Anti-Inflammatory Agents", Expert Opinion on Therapeutic Patents, 11(7):1137-1145 (2001)—Abstract, 3 pages.

Tarumoto, et al., Studies on toxicity of hydrocortisone 17-butyrate 21-propionate—1. Accute toxicity of hydrocortisone 17-butyrate 21-propionate and its analogues in mice, rats and dogs (author's trans), J Toxicol Sci., Jul. 1981; 6 Suppl: 1-16 (Abstract only).

Tata, et al., "Penetration of Minoxidil from Ethanol Propylene Glycol Solutions: Effect of Application Volume on Occlusion", Journal of Pharmaceutical Sciences, 84(6):688-691 (1995).

Torres-Rodriguez, JM., "New topical antifungal drugs," Arch Med Res. 1993 Winter; 24(4), pp. 371-375 (abstract).

Toxicology and Carcinogenesis Studies of t-Butyl Alcohol (CAS No. 75-65-0) in F344/N Rats and B6C3F1 Mice (Drinking Water Studies), http://ntp.niehs.nih.gob/?objectid-=0709F73D-A849-80CA-5FB784E866B576D1. Accessed Dec. 9, 2008, 4 pages.

Trofatter, "Imiquimod in clinical Practice", European Journal of Dermatology, 8(7 Supp.):17-19 (1998)—Abstract, 1 page.

Tsai, et al., "Drug and Vehicle Deposition from Topical Applications: Use of In Vitro Mass Balance Technique with Minosidil Solutions", J. Pharm. Sci., 81(8):736-743 (1992)—Abstract, 1 page.

Tsai, et al., "Influence of Application Time and Formulation Reapplication on the Delivery of Minoxidil through Hairless Mouse Skin as Measured in Franz Diffusion Cells", Skin Pharmacol., 7:270-277 (1994).

Tyring, "Immune-Response Modifiers: A New Paradigm in the Treatment of Human Papillomavirus", Current Therapeutic Research, 61(9):584-596 (2000)—Abstract, 1 page.

Uner, M. et al. "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel." Pharmazie. 60. 2005. 5 pages.

Veron, et al., "Stability of Minoxidil Topical Formulations", Ciencia Pharmaceutica, 2(6):411-414 (1992), Abstract, 1 page.

Williams, "Scale up of an olive/water cream containing 40% diethylene glycol momoethyl ether", Dev. Ind. Pharm., 26(1):71-77 (2000).

Wormser et al., Protective effect of povidone-iodine ointment against skin lesions induced by sulphur and nitrogen mustards and by non-mustard vesicants, Arch. Toxicol., 1997, 71, 165-170.

Wormser, Early topical treatment with providone-iodine ointment reduces, and sometimes prevents, skin damage following heat stimulus, Letter to the Editor, Burns 24, pp. 383, 1998.

Gill, A.M, et al., "Adverse Drug Reactions in a Paediatric Intensive Care Unit," Acta Paediatr 84:438-441, 1995.

Gladkikh, "Ascorbic Acid and Methods of Increasing its Stability in Drugs", Translated from Khimiko-Farmatsevticheskii Zhurnal, 4(12):37-42 (1970)—1 page.

Glaser, et al., Hyperhidrosis: A Comprehensive and Practical Approach to Patient Management, Expert Rev. Dermatol. 1(6), 773-775 (2006).

Groveman, et al., "Lack of Efficacy of Polysorbate 60 in the Treatment of Male Pattern Baldness", Arch Intern Med, 145:1454-1458 (1985).

Gschnait, F., et al., "Topical Indomethacin Protects from UVB and UVA Irriadiation," Arch. Dermatol. Res. 276:131-132, 1984.

Hakan, et al., "The protective effect of fish oil enema in acetic acid and ethanol induced colitis," The Turkish Journal of Gasroenterology, 2000, vol. 11, No. 2, pp. 155-161.

Harrison, et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, 38(9):2059-2064 (1994).

Koerber, S., "Humectants and Water Activity," Water Activity News, 2000, ISSN No. 1083-3943.

Li, et al., "Solubility Behavior of Imiquimod in Alkanoic Acids", Abstract 3029, Pharmaceutical Research, vol. 14, No. 11 Supplemental (November), p. S475 (1997), 2 pages.

Merriam Webster Online Dictionary [online] retrieved from http://www.merriam-webster.com/cgi-bin/dictionary?book=dictionary &va=derivative on Jul. 5, 2008; 1 page.

Merriam-Webster Online Dictionaary, 2008, "Mousse," Merriam-Webster Online, Dec. 8, 2008 http://www.merriam-webster.com/dictionary/mousse, 2 pages.

Olsen, et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, 57:767-774 (2007).

OM Cinnamate. http://www.makingcosmetics.com/sunscreens/OM-Cinnamate-p102.html accessed Sep. 26, 2009, 1 page.

Pakpayat, et al., "Formulation of Ascorbic Acid Microemulstions with Alkyl Polyglycosides", European Journal of Pharmaceutics and Biopharmaceutics, 72:444-452 (2009).

Paula. http://ww.cosmeticscop.com/cosmetic-ingredient-dictionary/definition/259/c12-15-alkyl-benzoate.aspx. Printed Oct. 24, 2010. 1 page.

Raymond, Iodine as an Aerial Disinfectant, Journal of Hygiene, vol. 44, No. 5 (May 1946), pp. 359-361.

Rosacea, http://clinuvel.com/skin-conditions/common-skin-conditions/rosacea#h0-6-prevention. Accessed Sep. 9, 2010, 5 pages.

Schmidt A., "Malassezia furfur: a fungus belonging to the physiological skin flora and its relevance in skin disorders," Curtis., Jan. 1997; 59(1), pp. 21-24 (abstract).

Sigma-Aldrich, Material Safety Data Sheet, Hydroxyethyl Cellulose, Mar. 3, 2004, 5 pages.

Stehle et al., Uptake of minoxidil from a new foam formulation devoid of propylene glycol to hamster ear hair follicles, *J. Invest. Dermatol.*, 2005, 124(4), A101.

Sweetman, Sean C. Martindale: The Complete Drug Reference. 33rd Edition. London. Pharmaceutical Press. Jun. 21, 2002. pp. 1073 and 1473. 5 pages.

Tadros, Tharwat F. "Surfactants in Nano-Emulsions." Applied Surfactants: Principles and Applications. Wiley-VCH Verlag GmbH & Co. Weinheim. ISBN: 3-527-30629-3. 2005. pp. 285-308.

Tata, et al., "Relative Influence of Ethanol and Propylene Glycol Cosolvents on Deposition of Minoxidil into the Skin", Journal of Pharmaceutical Sciences, 83(10):1508-1510 (1994).

Tsai, et al., "Effect of Minoxidil Concentration on the Deposition of Drug and Vehicle into the Skin", International Journal of Pharmaceutics, 96(1-3):111-117 (1993)—Abstract, 1 page.

Wermuth, C.G. "Similarity in drugs: reflections on analogue design," Drug Discovery Today, vol. 11, Nos. 7/8, Apr. 2006, pp. 348-354.

Karasu, T.B. et al., "Treatment of Patients with Major Depressive Disorder, Second Edition," pp. 1-78, 2000.

"Burn patients need vitamin D supplements." *Decision News Media*, Jan. 23, 2004, http://www.nutraingredients.com/Research/Burn-patients-need-vitamin-D-supplements, Accessed: May 5, 2010.

"Minocycline" accessed on Oct. 21, 2011 at en.wikipedia.org/wiki/Minocycline, 7 pages.

"Reaction Rate" Accessed at en.wikipedia.org/wiki/Reaction_rate on Dec. 18, 2011, 6 pages.

'Niram Chemicals' [online] Niram Chemicals, [retrieved on Jul. 17, 2012]. Retrieved from the Internet: <URL: http://www.indiamart.com/niramchemicals/chemicals.html>, 7 pages.

Barry and Badal, "Stability of minocycline, doxycycline, and tetracycline stored in agar plates and microdilution trays," *Current Microbiology*, 1978, 1:33-36.

Cheshire, et al., Disorders of Sweating, www.medscape.com, Semin Neurol 23(4):399-406, 2003.

Disorder. (2007). In the American Heritage Dictionary of the English Language. Retrieved from http://www.credoreference.com/entry/hmdictenglang/disorder. 1 page.

Hargreaves, "Chemical Formulation, An Overview of Surfactant-Based Preparations Used in Everyday Life", *The Royal Society of Chemistry*, pp. 114-115 (2003).

Hormones. Http://www.greenwillowtree.com/Page.bok?file=libido. html. Jan. 2001.

Hydroxyethylcellulose. Http: //terpconnect.umd.edu/-choi/MSDS/Sigma-Aldrich/HYDROXYETHYL%20CELLULOSE, 5 pages, Jan. 14, 2004.

Jan. "Troubled Times: Detergent Foam." http://zetatalk.com/health/theal17c.htm. Accessed Feb. 9, 2012. 2 pages.

Joseph, "Understanding foams & foaming," University of Minnesota (1997), at http://www.aem.umn.edu/people/faculty/joseph/archive/docs/understandingfoams.pdf, pp. 1-8.

Lebwohl et al., "A randomized, double-blind, placebo-controlled study of clobestasol propionate 0.05% foam in the treatment of nonscalp psoriasis," *International Journal of Dermatology*, 2002, 41(5):269-274.

Martindale. 33 ed. London, Bath Press, 2002. pp. 1073 and 1473.

Merck index, 10th edition, Merck & Co., Inc.: Rahway, NJ, 1983, pp. 39 (entry 242 for allantoin).

Merck index, 14th edition, O'Neill, ed., 2006, entry for p-amino benzoic acid.

Merck index, 14th edition, O'Neill, ed., 2006, entry for zinc oxide.

Metronidazole. www.usp.org/pdf/EN/veterinary/metronidazole.pdf. accessed Sep. 10, 2009, 4 pages.

Neutrogena. Http://www.cosmetoscope.com/2010/04/neutrogea-clinical-with-johnson-johnsons-cytomimic-techology/. Published Apr. 28, 2010. Accessed Sep. 11, 2010, 5 pages.

Oil. Dictionary of Chemistry. Editor: DWA Sharp. Copyright 1990.

Smith, Anne. "Sore Nipples." Breastfeeding Mom's Sore Nipples: Breastfeeding Basics. http://breastfeedingbasics.com/articles/sore-nipples. Accessed Feb. 8, 2012. 9 pages.

Surfactant. Chemistry Glossary. Http://chemistry.about.com/od/chemistryglossary/g/surfactant.htm, 2012, 1 page.

Third Party Submission for U.S. Appl. No. 12/014,088, Feb. 4, 2009, 4 pages.

Tzen, Jason T.C. et al. "Surface Structure and Properties of Plant Seed Oil Bodies." Department of Botany and Plant Sciences, University of California, Riverside, California 92521. Apr. 15, 1992. 9 pages.

Yamada and Chung, "Crystal Chemistry of the Olivine-Type Li($Mn_yFe_{1-y}$)$PO_4$ and ($Mn_yFe_{1-y}$)$PO_4$ as Possible 4 V Cathode Materials for Lithium Batteries," *J. Electrochemical Soc.*, 2001, 148(8): A960-967.

Material Safety Data Sheet, Progesterone, Apr. 26, 2006, 5 pages.

Nietz, "Molecular orientation at surfaces of solids," *J. Phys. Chem.*, 1928, 32(2): 255-269.

Padhi et al., "Phospho-olicines as positive-electrode materials for rechargeable lithium batteries," *J. Electrochemical Soc.*, 1997, 144(4): 1188-1194.

Ravet et al., "Electroactivity of natural and synthetic triphylite," *J. of Power Sources*, 2001, 97-98: 503-507.

Shrestha et al., Forming properties of monoglycerol fatty acid esters in nonpolar oil systems, *Langmuir*, 2006, 22: 8337-8345.

"Coal tars and coal-tar pitches," *Report on Carcinogens, Twelfth Edition*, 2011, 3 pages.

Adisen et al. "Topical tetracycline in the treatment of acne vulgaris," *J Drugs Dermatol.*, 2008, 7:953-5.

Baskaran et al., "Poloxamer-188 improves capillary blood flow and tissue viability in a cutaneous burn wound," *J. Surg. Res.*, 2001, 101(1):56-61.

Bell-Syer et al. "A systematic review of oral treatments for fungal infections of the skin of the feet," *J. Dermatolog. Treat.*, 2001, 12:69-74.

Boehm et al. 1994, "Synthesis of high specific activity [.sup.3 H]-9-cis-retinoic acid and its application for identifying retinoids with unusual binding properties," *J. Med. Chem.*, 37:408-414.

Carapeti et al., "Topical diltiazem and bethanechol decrease anal sphincter pressure and heal anal fissures without side effects," *Dis Colon Rectum*, 2000, 43(10):1359-62.

Cook and Mortensen, "Nifedipine for treatment of anal fissures," *Dis Colon Rectum*, 2000, 43(3):430-1.

Dumortier et al., "A review of poloxamer 407 pharmaceutical and pharmacological characteristics," *Pharmaceutical Res.*, 2006, 23(12):2709-2728.

Ebadi et al., "Healing effect of topical nifedipine on skin wounds of diabetic rats," *DARU*, 2003, 11(1):19-22.

Effendy and Maibach. "Surfactants and Experimental Irritant Contact Dermatitis." *Contact Dermatol.*, 1995, 33:217-225.

Elias and Ghadially, "The aged epidermal permeability barrier," *Clinical Geriatric Medicine*, Feb. 2002, pp. 103-120.

Fantin et al., "Critical influence of resistance to streptogramin B-type antibiotics on activity of RP 59500 (Quinupristin-dalfopristin) in experimental endocarditis due to *Staphylococcus aureus*," *Antimicrob Agents and Chemothery*, 1999, 39:400-405.

Fluter et al., "Glycerol accelerates recovery of barrier function in vivo," *Acta Derm. Venereol,.* 1999, 79:418-21.

Garti et al. "Sucrose Esters microemulsions," *J. Molec. Liquids*, 1999, 80:253-296.

Hammer et al. "Anti-Microbial Activity of Essential Oils and other Plant extracts," *J. Applied. Microbiology*, 1999, 86:985-990.

Hwang et al. "Isolation and identification of mosquito repellents in *Artemisia vulgaris*," *J. Chem. Ecol.*, 11: 1297-1306, 1985.

Knight et al., "Topical diltiazem ointment in the treatment of chronic anal fissure," *Br. J. Surg.*, 2001, 88(4):553-6.

Kucharekova et al., "Effect of a lipid-rich emollient containing ceramide 3 in experimentally induced skin barrier dysfunction," *Contact Dermatitis*, Jun. 2002, pp. 331-338.

Leive et al, "Tetracyclines of various hydrophobicities as a probe for permeability of *Escherichia coli* outer membrane," *Antimicrobial Agents and Chemotherapy*, 1984, 25:539-544.

Luepke and Kemper, "The HET-CAM Test: An Alternative to the Draize Eye Test," *FD Chem. Toxic.*, 1986, 24:495-196.

Osborne and Henke, "Skin Penetration Enhancers Cited in the Technical Literature," *Pharm. Technology*, Nov. 1997, pp. 58-86.

Padi. "Minocycline prevents the development of neuropathic pain, but not acute pain: possible anti-inflammatory and antioxidant mechanisms," *Eur J. Pharmacol*, 2008, 601:79-87.

Palamaras and Kyriakis, "Calcium antagonists in dermatology: a review of the evidence and research-based studies," *Derm. Online Journal*, 2005, 11(2):8.

Passi et al., Lipophilic antioxidants in human sebum and aging, *Free Radical Research*, 2002, pp. 471-477.

Perrotti et al., "Topical Nifedipine With Lidocaine Ointment vs. Active Control for Treatment of Chronic Anal Fissure," *Dis Colon Rectum*, 2002, 45(11):1468-1475.

Repa et al. "All-trans-retinol is a ligand for the retinoic acid receptors," *Proc. Natl. Acad Sci, USA*, 90: 7293-7297, 1993.

Ruledge, "Some corrections to the record on insect repellents and attractants," *J. Am. Mosquito Control Assoc*, 1988, 4(4): 414-425.

Sakai et al., "Characterization of the physical properties of the stratum corneum by a new tactile sensor," *Skin Research and Technology*, Aug. 2000, pp. 128-134.

Schaefer, "Silicone Surfactants," *Tenside, Surfactants, Deterg.*, 1990, 27(3): 154-158.

Simoni et al., "Retinoic acid and analogs as potent inducers of differentiation and apoptosis. New promising chemopreventive and chemotherapeutic agents in oncology," *Pure Appl Chem.*, 2001, 73(9):1437-1444.

Smith, "Hydroxy acids and skin again," *Soap Cosmetics Chemical Specialties*, 1993, pp. 54-59.

Solans et al. "Overview of basic aspects of microemulsions," Industrial Applications of Microemulsions, Solans et al Eds, New York, 1997, 66:1-17.

Squillante et al., "Codiffusion of propylene glycol and dimethyl isosorbide in hairless mouse skin," *European J. Pharm. Biopharm.*, 1998, 46(3):265-71.

Todd et al. "Volatile Silicone Fluids for Cosmetics," *91 Cosmetics and Toiletries*, 1976, 27-32.

Torma et al., "Biologic activities of retinoic acid and 3,4-dehydroretinoic acid in human keratinoacytes are similar and correlate with receptor affinities and transactivation properties," *J. Invest. Dermatology*, 1994, 102: 49-54.

USP23/NF 18 The United States Pharmacopeia: The National Formulary, US Pharmacopoeia, 1995, p. 10-14.

Van Slyke, "On the measurement of buffer values and on the relationship of buffer value to the dissociation constant of the buffer and the concentration and reaction of the buffer solution," *J. Biol. Chem.*, 1922, 52:525-570.

Van Cutsem et al., "The antiinflammatory efects of ketoconazole," *J. Am. Acad. Dermatol.*,1991, 25(2 pt 1):257-261.

Wang and Chen, "Preparation and surface active properties of biodegradable dextrin derivative surfactants," *Colloids and Surfaces A: Physicochemical and Engineering Aspects*, 2006, 281(1-3): 190-193.

Weindl et al., "Hyaluronic acid in the treatment and prevention of skin diseases: molecular biological, pharmaceutical and clinical aspects," *Skin Pharmacology and Physiology*, 2004, 17: 207-213.

Xynos et al., "Effect of nifedipine on rectoanal motility," *Dis Colon Rectum*, 1996, 39(2):212-216.

Yamada et al., "Candesartan, an angiotensin II receptor antagonist, suppresses pancreatic inflammation and fibrosis in rats," *J. Pharmacol. Exp. Ther.*, 2003, 307(1)17-23.

Paragraph E.3.1 of regulation (EC) No. 2003 (See Directive 67/548/EEC OJ 196, 16.8, 1967, p. 1.

Tzen et al., Lipids, proteins and structure of seed oil bodies from diverse species; *Plant Physiol.*, 1993, 101:267-276.

Brown et al. "Structural dependence of flavonoid interactions with Cu2+ inos: implications for their antioxidant properties," *Biochem. J.*, 1998, 330:1173-1178.

Cloez-Tayarani. et al., "Differential effect of serotonin on cytokine production in lipopolysaccharide-stimulated human peripheral blood mononuclear cells: involvement of 5-hydroxytryptamine2A receptors," *Int. Immunol.*, 2003, 15:233-40.

"Mineral oil USP," Chemical Abstracts Service Registry No. 8012-95-1, 2011, 7 pages.

"Tea tree oil," Chemical Abstract No. 68647-73-4, 2012, 2 pages.

Lin et al., "Ferulic acid stabilizes a solution of vitamins c and e and doubles its protoprotection of skin," *J Invest Dermatol*, 2005, 125:826-32.

\* cited by examiner

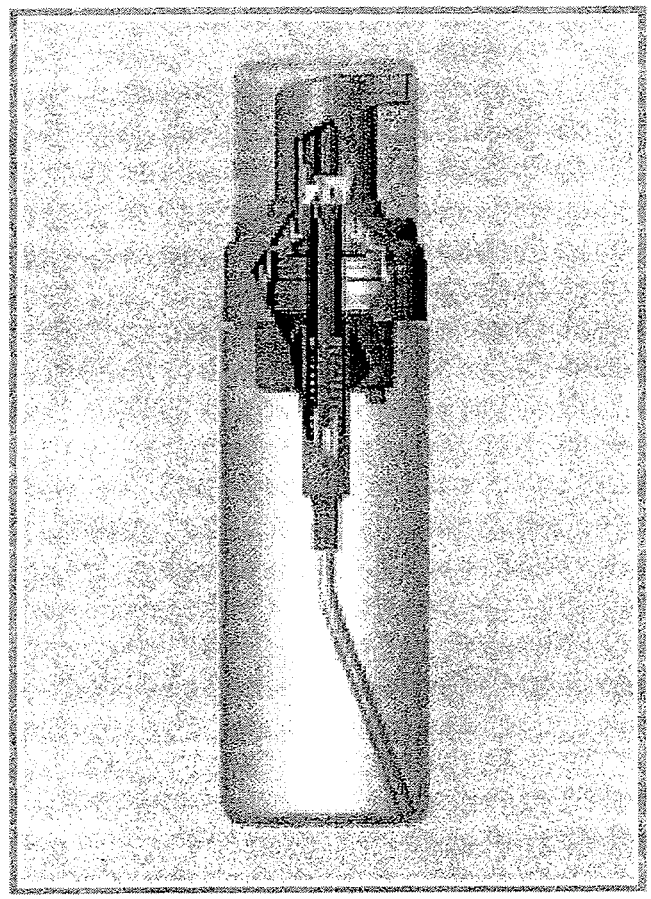

FOAMABLE COMPOSITIONS

RELATED APPLICATIONS

This application is a continuation of and claims the benefit of priority under 35 U.S.C. §120 to U.S. patent application Ser. No. 12/499,609, filed Jul. 8, 2009, entitled "Foamable Iodine Compositions," which claims the benefit of priority under 35 U.S.C. §120 to U.S. patent application Ser. No. 10/835,359, filed Apr. 28, 2004, entitled "Foamable Iodine Compositions," which claims the benefit of priority under 35 U.S.C. §119(e) to U.S. Provisional Patent Application No. 60/466,094, filed Apr. 28, 2003, entitled "Foamable Iodine Compositions," the entire contents of all of which are incorporated herein by reference.

FIELD OF THE INVENTION

The present invention relates to a foamable composition of matter comprising iodine. The invention further relates to compositions that, when provided in a suitable foaming system, evolve into foam, effective in the topical treatment of various skin conditions.

BACKGROUND OF THE INVENTION

Iodine and iodine complex preparations are widely employed as disinfectants in human and veterinary medicine. Iodine has a powerful bactericidal and fungicidal action and is also active against viruses. It is used as topical antiseptic agents for treatment of small wounds, abrasions and other skin lesions such as herpes simplex. Iodine containing compositions are used for protective treatment of a skin area to be dissected.

Iodine preparations are used in veterinary medicine as post-milking disinfecting treatment of the udders. Iodine is also effectively used for disinfection of drinking water and swimming pool water (*Martindale, The extra pharmacopoeia, [28TH] edition*, Eds.: Reynolds, J. E. F. and Prasad, A. B., *The Pharmaceutical Press, London*, 1982, pp. 862-864).

Topical iodine preparations possess counter-irritating activity in rheumatism, tenosynovitis and in inflammatory diseases of the peripheral nervous system and muscles. Additional pronounced counter-irritating activity of iodine was demonstrated against skin irritation caused by chemical and thermal stimuli. Iodine is also effective against other skin irritants such as mechlorethamine, divinylsulfone, iodoacetic acid and cantharidine (Wormser et al. *Arch. Toxicol.* (1997) 71, 165-170).

Molecular iodine ($I_2$) is practically water insoluble unless iodide (sodium or potassium salts) is present in the solution to form the water-soluble ion ($I_3^-$). Iodine can be dissolved in ethanol but precipitates in the presence of water. Thus, iodine tincture (which contains ethyl alcohol and water) must also contain iodide to form $I_3^-$ for proper dissolution.

Iodine formulations using other solvents or carriers are known. In some cases, these formulations are shown to have greater iodine solubility or improved iodine release. In some cases, the iodine formulations are demonstrated to be more potent as antiseptics than currently available commercial iodine preparations.

Post-exposure treatment with topical povidone (polyvinylpyrolidone)-iodine preparation has been shown to provide significant protection against mustard gas (sulfur mustard, SM)-induced skin lesions (Wormser et al. *Arch. Toxicol.* (1997) 71, 165-170). Studies also have shown the counter-irritating activity of povidone-iodine against thermal stimuli in humans (Wormser, *Burns* (1998) 24, 383). The experience with patients after accidental heat burns (mostly of grade I; caused by hot water or oil or by hot steam) has shown that topical application of povidone-iodine ointment immediately after the stimulus reduced the degree of skin lesions. The shorter the interval between stimulus and treatment the better the protection achieved.

U.S. Pat. No. 5,071,648 discloses a composition containing acetalized polyvinyl alcohol complexed with iodine, which releases free iodine in the presence of water.

WO 01/70242 discloses a composition including molecular iodine and tetraglycol (TG) that facilitates the dissolution of iodine, enhances its antiseptic effect, and remains stable in the presence of water, in contrast to other iodine solvents, such as ethanol, in which iodine precipitates after water addition. Povidone-iodine complex (PVP-I) may also be dissolved in TG or a TG water system. A pharmaceutically acceptable vehicle according to WO 01/70242 includes an oil/water or a water/oil emulsion, a solution, a suspension, a gel, an ointment, a patch, or an aerosol, preferably solutions, gels and washable ointments.

Despite many years of usage in topical therapy, iodine compositions are still restricted to the conventional list of dosage forms, consisting of water/oil emulsions, solutions, suspensions, gels, ointments, patch, or aerosols. All these preparations comprise liquid or semi-liquid substances, having continuous texture and consistency and possessing specific gravity of 0.7-1.1. Such preparations are disadvantageous, when intended to treat relatively large areas. They are even more disadvantageous when the area to be treated is sensitive, such as area with burns or open wounds, where rubbing a liquid or semi-solid formulation is difficult and painful.

Certain foamable formulations are known in the art.

U.S. Pat. No. 5,716,611 discloses a topical formulation comprising an anti-microbially effective amount of povidone-iodine and from 2% to about 30% of a water-soluble emollient comprising from about 1 to about 99% ethoxylated higher aliphatic alcohol and from about 1 to about 99% ethoxylated cholesterol derivative. The composition includes thickening agents and surfactants that provide foaming upon rubbing on the applied surface.

U.S. Pat. No. 6,258,374 provides a pharmaceutical composition for rectal or vaginal application containing at least two parts wherein the composition comprises (i) two or more physiologically acceptable substances each in separate parts of the composition which are such that on admixture they react to produce a physiologically acceptable gas; (ii) in at least one part of the composition a polymer stabilizer which is adapted to facilitate the formation of a water-soluble collapsible foam structure; and (iii) in at least one part of the composition a pharmaceutically active substance. One of the optional active substances is iodine.

International patent application WO 96/19921 discloses a composition having biocidal activity comprising an active agent selected from iodine or a compound or complex thereof and a polymeric solubilizing agent. The composition may be a foam.

U.S. Pat. No. 6,187,290 teaches physiologically acceptable foam including a foamable carrier separately packaged from an active ingredient. The active ingredient may be, among others, povidone-iodine. Surfactants, humectants and plasticizers may be optionally included.

U.S. Pat. No. 5,951,993 discloses a composition including a lower alcohol and water in a weight ratio of about 35:65 to 100:0, and a thickener system. The thickener system includes at least two emulsifiers, each emulsifier containing at least one hydrophobic group and at least one hydrophilic group. The composition optionally contains iodine or a complexed form of iodine. The composition is useful as a presurgical scrub replacement, a lotion or other hand preparation.

U.S. Pat. No. 5,672,634 describes a rigid, cellular PVP-I foam product, useful as an iodophor, containing about 0.1-2% cross linker and about 16-18% total inorganic iodine.

U.S. Pat. No. 5,545,401 teaches a foaming gel consisting essentially of water, povidone and iodine. In one embodiment water is added to the gel in a closed container pressurized at between 1 and 3 atmospheres with pentane so that when the mixture is returned to atmospheric pressure it spontaneously forms a foam.

U.S. Pat. No. 5,254,334 describes an anhydrous cream composition comprising (a) glycerin in an amount from about 40% to about 60% by weight based on the weight of the total composition; (b) sodium cocoyl isethionate in an amount from about 10 to about 19% by weight based on the weight of the total composition; (c) emollients in an amount from about 10 to about 40% by weight based on the weight of the total composition; and (d) sodium lauryl sulfate in an amount from about 1 to about 5% by weight based on the weight of the total composition. The composition may further comprise a foam booster or active ingredients such as PVP-iodine.

U.S. Pat. No. 4,271,149 discloses a germicidal iodine composition containing an aqueous solution of elemental iodine and at least one organic substance which slowly reacts with iodine selected from the group consisting of iodine complexing polymers, surface active agents, alcohols, polyols and water soluble solvents. The iodine composition is stable for extended storage by providing balanced sources of iodide ion in the range of about 0.025% to 0.5% and iodate ion in the range of about 0.005% to 0.2% while maintaining a pH within the range of pH 5-7. Foam stabilizers are optional components of the composition.

New topical dosage forms are desired to deliver iodine and to treat skin conditions that respond to iodine topical application. A simple-to-use breakable foam, having low specific gravity and being easily spreadable on large skin areas, is particularly desirable.

SUMMARY OF THE INVENTION

The present invention provides a foamable composition including iodine, water, a foam adjuvant, a surface-active agent and a gelling agent that is easily applied and provides high availability of iodine to the applied surface.

According to one aspect the present invention, a foamable composition includes iodine, water, a foam adjuvant, a surface active agent and a gelling agent, in the following concentrations:

about 0.1% to about 5% by weight iodine;
about 80% to about 99.6% by weight of at least one solvent;
about 0.1% to about 5% by weight of at least one foam adjuvant;
about 0.1% to about 5% by weight of at least one surface active agent; and
about 0.1% to about 5% by weight of at least one gelling agent.

The % values presented herein are provided on a weight (w/w) basis of the total composition.

The composition according to one or more embodiments of the present invention, when provided in a suitable foaming device, forms a foam that is effective in the topical treatment of various skin conditions.

According to one or more embodiments of the present invention, the composition is provided in a plastic or glass propellant free foaming dispenser and forms a breakable or collapsible foam when dispensed from the propellant free foaming dispenser.

According to one or more embodiments of the present invention, the composition further includes a liquefied or compressed gas propellant, for example, at a concentration of about 3% to about 25% of the total composition.

According to one or more embodiments of the present invention, the foamed composition has specific gravity of about 0.02 gr/ml to about 0.35 gr/ml.

According to one or more embodiments of the present invention, iodine is selected from molecular iodine and complexed iodine. Complexed iodine may be selected from cadexomer-iodine, diiodhydrin, domiodol, hydriodic acid, iodinated glycerol, iodoform, iodide and povidone-iodine According to one or more embodiments of the present invention, the solvent is water or a water miscible organic solvent, such as a polyhydroxy compounds and poly-ethoxylated compounds. In one embodiment the composition has a water-to-water miscible organic solvent ratio of about 1:10 to about 10:1. Due to the skin irritability of lower alkyl alcohols, the water miscible compound is not a lower alkyl, e.g., $C_1$-$C_5$, alcohol.

In one or more embodiments, the polyhydroxy compound is selected from ethylene glycol, propylene glycol, glycerol, butanediols and isomers thereof, pentaerythritol, sorbitol, mannitol, dimethyl isosorbide, polyethylene glycol, polypropylene glycol, diethylene glycol monoethyl ether and mixtures thereof.

In one or more embodiments, the poly-ethoxylated compound is selected from polyethylene glycol, tetrahydrofurfuryl alcohol and polyethyleneglycol. The solvent can be mixtures of water, polyhydroxy compounds and/or poly-ethyoxylated compounds.

According to one or more embodiments, a surface active agent may be an anionic surface active agent, a cationic surface active agent, a nonionic surface active agent, a zwitterionic surface active agent, an amphoteric surface active agent, an ampholytic surface active agent and mixtures thereof.

In one or more embodiments, the surface-active agent includes at least a non-ionic agent. In one or more embodiments, the surface active agent is a mixture of a non-ionic surface active agent and an anionic surface active agent provided at a weight ratio of about 4:1 to about 1:4 more preferably a weight ratio of about 2:1 to about 1:2. In one or more embodiments, the surface-active agent has a HLB value higher than about 8.

According to one or more embodiments, the foam adjuvant is selected from a fatty alcohol, a fatty acid mixtures thereof, and is provided at a concentration between about 0.4% and about 2.5% of the composition.

Another aspect the present invention provides a method of treating, alleviating or preventing a human or veterinary disorder by topically administering to a surface afflicted with the disorder an effective amount of the composition according to one or more embodiments of the present invention.

The method of the invention, according to one or more embodiments, provides for the prophylaxis, or treatment of or alleviation of the symptoms of a variety of infectious dermatological disorders, including for example heat burns, chemical burns, infections, wounds, cuts and ulcers and radioactive radiation damage, and burns and infections resulting from chemical and biological warfare agents.

BRIEF DESCRIPTION OF THE DRAWING

The invention is described with reference to the FIGURE, which is provided for the purpose of illustration only and is not intended to be limiting of the invention.

The FIGURE is an illustration of a foam dispenser used in one or more embodiments of the present invention.

DETAILED DESCRIPTION OF THE INVENTION

Composition

According to one aspect, the present invention provides a foamable composition of matter includes iodine, water, a foam adjuvant, a surface active agent and a gelling agent, in the following concentrations, reported as percent by weight:
 iodine: about 0.1% to about 5%;
 at least one solvent: about 80% to about 99.6%;
 at least one foam adjuvant: about 0.1% to about 5%;
 at least one surface active agent: about 0.1% to about 5%; and
 at least one gelling agent: about 0.1% to about 5%.
The % values presented herein are provided on a weight (w/w) basis of the total composition.

The composition according to one or more embodiments of the present invention is applied to the surface as a foam. That is, the foamed composition is applied to the substrate and is not generated by rubbing or lathering. The foamed composition, according to one or more embodiments of the present invention, is dispensed from a glass or plastic container that dispenses foam in the absence of a gas or liquid propellant.

Alternatively, the composition of the present invention further includes a liquefied or compressed gas propellant at a concentration of about 3% to about 25% of the total composition. Examples of suitable propellants include volatile hydrocarbons such as butane, propane, isobutane or mixtures thereof, and fluorocarbon gases.

The foamed composition, according to one or more embodiments of the present invention, is of exceptionally low specific gravity, for example, the foamed composition has a specific gravity in the range of about 0.02 gr/ml to about 0.35 gr/ml. Although of low specific gravity, the foam is highly stable and will remain without collapse for several minutes. Nonetheless, the foam collapses readily upon application of mild shear stress. Low specific gravity, high foam stability and ready collapsibility all contribute to a foamed composition that is easily applied and administered over large areas without rubbing or chaffing of the affected area.

Iodine

"Iodine" and "iodine species" include iodine in its native form or released from a compound. In its native form, iodine ($I_2$) is provided as bluish-black crystals, having density of about 5 $g/cm^3$. When used as is, the iodine concentration in the total composition ranges between 0.1% and 5% and more preferably, between 0.5% and 1.5%. In other embodiments of the present invention molecular iodine is released from an iodine-containing and/or producing compound. Non-limiting examples of such compounds include cadexomer-iodine, diiodhydrin, domiodol, hydriodic acid, iodinated glycerol, iodide, iodoform, and povidone-iodine. When provided as an iodine-containing and/or producing compound, the compound concentration in the total composition is calculated to achieve a final iodine concentration ranging between about 0.1% and 5% by weight and more preferably, between about 0.5% and about 1.5% by weight.

Solvent

According to one or more embodiments, the composition includes about 80% to about 99.6% solvent, and typically includes water. Iodine is not highly soluble in water and thus, formulation stability and effectiveness is limited. In a one or more embodiments of the present invention, the solvent includes water and a water miscible organic solvent, which by way of non-limiting examples, is a polyhydroxy compound and/or a poly-ethoxylated compound.

Suitable polyhydroxy solvents (polyols) include small organic molecules having two or more hydroxy groups on their carbon skeleton, such as ethylene glycol, propylene glycol, glycerol, butanediols and isomers thereof, pentaerythritol, sorbitol, mannitol, dimethyl isosorbide, polyethylene glycol, polypropylene glycol, diethylene glycol monoethyl ether (Transcutol®) and mixtures thereof.

Poly-ethoxylated compounds can enhance the effectiveness of iodine significantly by dissolving the $I_2$. Examples of suitable poly-ethoxylated compounds include polyethylene glycol (e.g., PEG 400), tetrahydrofurfuryl alcohol polyethyleneglycol ether (glycofurol, tetraglycol (TG)). Among the above-mentioned water miscible solvents, suitable compounds include transcutol, polyethylene glycol and TG and mixtures thereof. The ratio between water and the water miscible solvents is in the range of about 1:10 to about 10:1. In one or more embodiments, the ratio is between about 1:4 and about 4:1. Due to the skin irritability of lower alkyl (C1-C5) alcohols, and the tendency of such alcohols to impair the natural skin barrier by dissolving and removing the oily components of the skin, lower alkyl alcohols are not included as a miscible organic solvent.

Foam Adjuvant

A foam adjuvant is included in the composition to improve the stability and reduce the specific gravity of the foamed composition. In one or more embodiments of the present invention, foam adjuvants include fatty alcohols, fatty acids, and mixtures thereof. The foam adjuvant can include at least one fatty alcohol and at least one fatty acid.

Suitable fatty alcohols include alcohols having 15 or more carbons in their carbon chain, such as cetyl alcohol and stearyl alcohol (or mixtures thereof). Other examples of fatty alcohols are arachidyl alcohol (C20), behenyl alcohol (C22), 1-triacontanol (C30), as well as alcohols with longer carbon chains (up to C50). The concentration of the fatty alcohol required to support the foam system is inversely related to the length of its carbon chains. Fatty alcohols that are derived from beeswax, including a mixture of alcohols, a majority of which has at least 20 carbon atoms in their carbon chain, are especially well suited as foam adjuvants according to the present invention. The concentration of the fatty alcohol required to support the foam system is inversely related to the length of its carbon chains.

Suitable fatty acids include acids having 16 or more carbons in its carbon chain, such as hexadecanoic acid (C16) stearic acid (C18), arachidic acid (C20), behenic acid (C22), octacosanoic acid (C28), as well as fatty acids with longer carbon chains (up to C50), or mixtures thereof. As for fatty alcohols, the concentration of fatty acids required to support the foam system is inversely proportionate to carbon chain length.

Optionally, the carbon atom chain of the fatty alcohol or the fatty acid may have at least one double bond. A further class of foam adjuvant agent includes a long chain fatty alcohol or fatty acid, wherein the carbon atom chain is branched. The carbon chain of the fatty acid or fatty alcohol can be substituted with a hydroxyl group, such as 12-hydroxy stearic acid.

The foam adjuvant of the present invention may include a mixture of fatty alcohols, fatty acids and hydroxy fatty acids and alcohols in any proportion. The total amount of foam adjuvants is about 0.1% to about 5% (w/w) of the carrier mass, and typically, the total amount is about 0.4% to about 2.5% (w/w) of the carrier mass.

In one or more embodiments of the present invention, a fatty alcohol possesses a therapeutic properties per se. Long chain saturated and mono unsaturated fatty alcohols, e.g., stearyl alcohol, erycyl alcohol, arachidyl alcohol and docosanol have been reported to possess antiviral, anti infective, anti-proliferative and anti-inflammatory properties (U.S. Pat. No. 4,874,794). Longer chain fatty alcohols, e.g., tetracosanol, hexacosanol, heptacosanol, octacosanol, triacontanol, etc. are also known for their metabolism modifying properties and tissue energizing properties. Long chain fatty acids have also been reported to possess anti-infective characteristics. Thus, the iodine foamable composition of the present invention, containing the foam adjuvant provides a synergistic therapeutic benefit in comparison with currently used vehicles, which are inert and non-active.

Surface-active Agent

According to one or more embodiments of the present invention, the surface-active agent includes any agent linking oil and water in the composition, e.g., the agent can be a surfactant. In one or more embodiments of the present invention, the composition includes about 0.1% to about 5% of the surface-active agent.

Suitable surface-active agents include anionic, cationic, nonionic, zwitterionic, amphoteric and ampholytic surfactants, as well as mixtures of these surfactants. Such surfactants are well known to those skilled in the pharmaceutical and cosmetic formulation art. Non-limiting examples of useful surfactants include sucrose esters, sorbitan esters, PEG esters or ethers of fatty chains, mono or diglycerides, isoceteth-20, sodium methyl cocoyl taurate, sodium methyl oleoyl taurate, sodium lauryl sulfate, triethanolamine lauryl sulfate and betaines (e.g., cocamidopropyl betaine and lauramidopropyl betaine), which are known to contribute to foam stability (foam boosters).

While any surface-active agent may be used in the present invention, a surface-active agent having an HLB (hydrophilic-lipophilic balance) higher than 8 is used in one or more embodiments of the present invention.

Non-ionic surfactants are particularly well suited as surface-active agents. A combination of a non-ionic surfactant and an anionic surfactant (such as sodium lauryl sulfate) may also be used. A ratio of non-ionic surfactant to anionic surfactant between around 4:1 and about 1:4, or between about 2:1 and about 1:2, provides a foam, which upon rubbing onto the skin collapses easily, to allow facile spreading and absorption. A surface-active agent mix is even further improved when a foam stabilizing surfactant, such as cocamidopropyl betaine, is added.

Gelling Agent

In one or more embodiments of the present invention, the composition includes about 0.1% to about 5% of a gelling agent. Suitable gelling agents include, in a non-limiting manner, naturally-occurring polymeric materials such as locust bean gum, guar gum, sodium alginate, sodium caseinate, egg albumin, gelatin agar, carrageenin gum, sodium alginate, xanthan gum, quince seed extract, tragacanth gum, starch, chemically modified starches and the like, semi-synthetic polymeric materials such as cellulose ethers (e.g. hydroxyethyl cellulose, methyl cellulose, carboxymethyl cellulose, hydroxy propylmethyl cellulose), hydroxypropyl guar gum, soluble starch, cationic celluloses, cationic guars and the like and synthetic polymeric materials such as carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like.

Also useful herein are gelling agents such as the acrylic acid/ethyl acrylate copolymers and the carboxyvinyl polymers sold, for example, by the B.F. Goodrich Company under the trademark of Carbopol® resins. These resins include a colloidal water-soluble polyalkenyl polyether cross linked polymer of acrylic acid cross linked with from 0.75% to 2% of a cross linking agent such as polyallyl sucrose or polyallyl pentaerythritol. Examples include Carbopol 934, Carbopol 940, Carbopol 950, Carbopol 980, Carbopol 951 and Carbopol 981. Carbopol 934 is a water-soluble polymer of acrylic acid cross linked with about 1% of polyallyl ether of sucrose having an average of about 5.8 allyl groups for each sucrose molecule.

Methods of Evolving and Releasing the Foam

Any customary method of evolving foam is applicable according to the present invention. By way of example, in one optional configuration, the composition according to one or more embodiments of the present invention is preferably placed, together with a liquefied or compressed gas propellant in the amount of about 3% to about 25% of the total composition, in an aerosol container. Upon pressing the actuator, a breakable foam, suitable for topical administration is released. Due to the oxidizing nature of iodine, containers that are coated with highly durable lacquers of coatings are used.

In an alternative exemplary configuration, the composition according to one or more embodiments of the present invention is placed in a plastic or glass container, equipped with a foaming dispenser that works without gas propellants. Such dispensers are described, for example, in U.S. Pat. No. 6,536,629, in which the dispenser includes a container and a dispensing assembly coupled in liquid-tight manner. The dispensing assembly can have a liquid pump with a liquid inlet and a liquid outlet. An exemplary foam dispenser is shown in the FIGURE.

Foam Characteristics

The foam that is released from the aerosol container or from the propellant-free foaming dispenser is well aerated. It has specific gravity of about 0.02 gr/ml to about 0.35 gr/ml. When applied onto a surface, specifically a skin surface, and rubbed gently, it spreads easily over the area, without the need of extensive rubbing.

A foam composition of one or more embodiments of the present invention is advantageous over formulation options. A foamed composition may possess one or more of the following properties. The foam is lightweight and thus, economical. The foam is easily spreadable, allowing treatment of large areas such as the arms, back, legs and the breast. The flow properties provide a foam that spreads effectively into folds and wrinkles, providing uniform distribution of the active agent without the need of extensive rubbing and absorbs into the skin. The low specific gravity, e.g., fluffy, nature of the foam renders application of the foam on large skin areas very easy, irritation-free and painless.

Foam Applications

The compositions according to one or more embodiments of the present invention are useful in the various medicinal disciplines including human and veterinary medicine. More generally, the compositions according to the present invention can be used in situations where use of iodine is preferred including, but not limited to, medicine, industrial processes, diagnostics and environmental purposes.

Specifically, the compositions according to one or more embodiments of the present invention are useful as antiseptic compositions. The compositions may be further used to protect from, prevent, alleviate the symptoms of or cure a variety of infectious dermatological disorders, including: bacterial Infections including cellulitis, acute lymphangitis, lymphadenitis, erysipelas, cutaneous abscesses, necrotizing subcutaneous infections, staphylococcal scalded skin syndrome, folliculitis, furuncles, hidradenitis suppurativa, carbuncles, paronychial infections, erythrasma; fungal infections including dermatophyte infections, yeast infections; parasitic infections including scabies, pediculosis, creeping eruption and viral infections.

The treatment of heat burns, chemical burns (caused by chemicals such as acids, bases, caustic materials and warfare chemicals), wounds, cuts and ulcers using the composition according to one or more embodiments of the present invention is particularly advantageous. Upon application, the foam spreads easily, covering the surface of the affected area, and without causing pain.

The composition of the invention is also useful as a protectant in case of exposure to radiation and radioactive isotopes.

According to another aspect the present invention provides a method of treating, alleviating or preventing a human or veterinary disorder by topically administering to a surface afflicted with the disorder an effective amount of the composition including:
- about 0.1% to about 5% by weight iodine;
- about 80% to about 99.6% by weight of at least one solvent;
- about 0.1% to about 5% by weight of at least one foam adjuvant;
- about 0.1% to about 5% by weight of at least one surface active agent; and
- about 0.1% to about 5% by weight of at least one gelling agent.

The present invention provides for the prophylaxis, or treatment of or alleviating the symptoms of a variety of infectious dermatological disorders, including heat burns, chemical burns, infections, wounds, cuts and ulcers and radioactive radiation damage, and burns and infections resulting from chemical and biological warfare agents.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

Foamable Iodine Composition

The table below lists the components of the foamable composition.

| Ingredient | % (w/w) | Function |
|---|---|---|
| Iodine ($I_2$) | 1% | Active agent |
| Purified Water | 64.3% | Water |
| Glycofurol | 30% | Water miscible solvent |
| Stearyl alcohol | 1% | Foam adjuvant |
| Sodium Lauryl Sulfate | 1% | Surface active agent |
| Sucrose Ester 70 | 1% | Surface active agent |
| Cocamidopropyl Betaine | 0.5% | Surface active agent |
| Methocel LV15 (Hydroxypropylmethyl cellulose) | 0.8% | Gelling agent |
| Xanthan Gum | 0.4% | Gelling agent |

Iodine was dissolved in a mixture of glycofurol and stearyl alcohol and the mixture was heated to ~60 C until homogeneity was obtained. Methocel was dispersed in one third portion of water, preheated to 80° C., and sucrose ester was added. The remaining two-third portion of water at room temperature was added under vigorous stirring; and xanthan gum and sodium lauryl sulfate and cocamidopropyl betaine were added mixing continuously for 15 minutes under vigorous stirring. The iodine mixture was added carefully to aqueous mixture and was stirred for an additional 5 minutes for complete homogeneity. The resultant product was cooled to room temperature and filled into bottles.

EXAMPLE 2

Pressurized Foam Comprising Iodine

The composition of Example 1 (50 ml) at ambient temperature was added to a 125 ml aerosol container, the container was sealed with an aerosol valve and a butane/propane propellant (about 16% of the composition mass) was compressed into the container. Upon pressing the aerosol valve, a rich foam having specific gravity of about 0.1 gr/ml was released.

EXAMPLE 3

Iodine Non-pressurized Foam

The composition of Example 1 (50 ml) at ambient temperature was added to a 125 ml container, equipped with a foaming dispenser that works without gas propellants (Airspray International Inc., 3768 Park Central Blvd. North, Pompano Beach, Fla. 33064, USA). Upon pressing the aerosol valve, rich foam having specific gravity of about 0.1 gr/ml to about 0.3 gr/ml was released.

The invention claimed is:

1. A non-irritating foamable composition in an aerosol container comprising:
   a carrier composition comprising:
   a. about 80% to about 99.6% by weight of the carrier composition of a solvent comprising water and a water miscible organic solvent;
   b. about 0.1% to about 5% by weight of the carrier composition of at least one foam adjuvant, wherein the at least one foam adjuvant is selected from a fatty alcohol, a fatty acid, a hydroxy fatty acid, and mixtures thereof;

c. about 0.1% to about 5% by weight of the carrier composition of at least one surface active agent; and a liquefied or compressed gas propellant wherein the weight ratio of the propellant to the carrier composition is about 3:97 to about 25:75;

wherein upon release from the container, the foamable composition forms a thermally stable breakable foam having a specific gravity of between about 0.02 g/mL and about 0.35 g/mL.

2. The foamable composition of claim 1, wherein the water miscible organic solvent is selected from the group consisting of a polyhydroxy solvent and a poly-ethoxylated compound.

3. The composition of claim 2, wherein the polyhydroxy solvent is selected from the group consisting of ethylene glycol, propylene glycol, glycerol, butanediols and isomers thereof, pentaerythritol, sorbitol, mannitol, dimethyl isosorbide, polyethylene glycol, polypropylene glycol, diethylene glycol monoethyl ether, and mixtures thereof; and, wherein the poly-ethoxylated compound is selected from the group consisting of polyethylene glycol, tetrahydrofurfuryl alcohol, and polyethyleneglycol.

4. The composition of claim 1, wherein the water to water miscible organic solvent ratio is in the range of about 1:10 to about 10:1.

5. The composition of claim 1, further comprising an iodine.

6. The composition of claim 1, having a specific gravity of about 0.02 gr/ml to about 0.35 gr/ml.

7. The composition of claim 1, wherein the at least one surface active agent is selected from the group consisting of anionic surface active agents, cationic surface active agents, non-ionic surface active agents, zwitterionic surface active agents, amphoteric surface active agents, ampholytic surface active agents, and mixtures thereof.

8. The composition of claim 7, wherein the at least one surface active agent is a mixture of a non-ionic surface active agent and an ionic surface active agent.

9. The composition of claim 8, wherein the non-ionic surface active agent to ionic surface active agent weight ratio is in the range of about 4:1 to about 1:4.

10. The composition of claim 8, wherein the non-ionic surface acting agent to ionic surface acting agent weight ratio is in the range of about 2:1 to about 1:2.

11. The composition of claim 7, wherein the at least one surface active agent has a HLB value higher than about 8.

12. The composition of claim 1, wherein the at least one foam adjuvant is present at about 0.4% to about 2.5% by weight of the carrier composition.

13. The composition of claim 1, wherein the at least one surface active agent is a non-ionic surface active agent.

14. The composition of claim 8, wherein the ratio of non-ionic to ionic surface active agent is about 3:2.

15. The composition of claim 8, wherein the ionic surface active agent comprises a zwitterionic surface active agent and the ratio of zwitterionic to non-ionic surface active agent is about 1:2.

16. The composition of claim 8, wherein the ionic surface active agent comprises an anionic surface active agent and the amount of anionic surface active agent is about the same as or is less than the amount of non-ionic surface active agent.

17. The composition of claim 1, further comprising about 0.1% to about 5% by weight of at least one gelling agent.

18. The composition of claim 17, wherein the at least one gelling agent comprises one or more of a naturally-occurring polymeric material, a chemically modified starch, a semi-synthetic polymeric material, a synthetic polymeric material, an acrylic acid/ethyl acrylate copolymer, or a carboxyvinyl polymers.

19. The composition of claim 17, wherein the at least one gelling agent comprises a locust bean gum, a guar gum, sodium alginate, sodium caseinate, an egg albumin, a gelatin agar, a carrageenin gum, a xanthan gum, a quince seed extract, a tragacanth gum, a starch, a cellulose ether, a hydroxypropyl guar gum, a soluble starch, a cationic cellulose, a cationic guar, a carboxyvinyl polymer, polyvinylpyrrolidone, polyvinyl alcohol, a polyacrylic acid polymer, a polymethacrylic acid polymer, a polyvinyl acetate polymer a, a polyvinyl chloride polymer, a polyvinylidene chloride polymer, a polyalkenyl polyether cross-linked polymer of acrylic acid, or any mixture of two or more thereof 20. The composition of claim 17, wherein the at least one gelling agent comprises a hydroxypropylmethyl cellulose, a hydroxyethyl cellulose, a methyl cellulose, a carboxymethyl cellulose, or any mixture of two or more thereof.

21. The composition of claim 5, wherein the iodine is selected from native iodine and complexed iodine or comprises both.

22. The composition of claim 21, wherein the complexed iodine is selected from the group consisting of cadexomeriodine, diiodhydrin, domiodol, hydriodic acid, iodinated glycerol, iodoform, povidone-iodine, and mixtures of any two or more thereof.

\* \* \* \* \*